(12) United States Patent
Lockwood et al.

(10) Patent No.: US 9,795,761 B2
(45) Date of Patent: Oct. 24, 2017

(54) MEDICAL KIT, PACKAGING SYSTEM, INSTRUCTION INSERT, AND ASSOCIATED METHODS

(75) Inventors: Robert Lockwood, Libertyville, IL (US); Jennifer E. Tomes, Mundelein, IL (US); Sarah Zyburt, Chicago, IL (US); Susan E. Macinnes, Cary, IL (US)

(73) Assignee: Medline Industries, Inc., Northfield, IL (US)

(*) Notice: Subject to any disclaimer, the term of this patent is extended or adjusted under 35 U.S.C. 154(b) by 107 days.

(21) Appl. No.: 13/153,265

(22) Filed: Jun. 3, 2011

(65) Prior Publication Data

US 2011/0232234 A1 Sep. 29, 2011

Related U.S. Application Data

(63) Continuation-in-part of application No. 12/495,148, filed on Jun. 30, 2009, now Pat. No. 8,631,935, and
(Continued)

(51) Int. Cl.
*B65D 69/00* (2006.01)
*B65D 71/00* (2006.01)
(Continued)

(52) U.S. Cl.
CPC ........... *A61M 25/002* (2013.01); *A61B 50/30* (2016.02); *A61B 50/33* (2016.02); *A61M 25/00* (2013.01);
(Continued)

(58) Field of Classification Search
CPC ....... A61M 25/002; A61B 50/30; A61B 50/33
(Continued)

(56) References Cited

U.S. PATENT DOCUMENTS 2,659,485 A 11/1953 Duley et al.
2,715,296 A * 8/1955 Pettit .............................. 446/418
(Continued)

FOREIGN PATENT DOCUMENTS

CN 201823147 5/2011
EP 2007/045943 4/2007
(Continued)

OTHER PUBLICATIONS

Dictionary definition m-w. URL:<http://www.merriam-webster.com/dictionary/brave>. Retrieved from Internet Dec. 10, 2013.*
(Continued)

*Primary Examiner* — Christopher L Gilligan
(74) *Attorney, Agent, or Firm* — Philip H. Burrus, IV

(57) ABSTRACT

Printed instructions can be included with the tray in a medical procedure kit.—The printed instructions can include instructional material, such as pictorial, step-by-step instructions intended for a health care services provider for using the medical procedure kit. The printed instructions can also include a separate patient aid, suitable for inclusion within the medical procedure kit, which includes patient education information relating to a particular medical procedure. To make recognition easier, the patient aid can be configured with a greeting card appearance, activity sheet appearance, or other graphical indicia that indicates that the patient aid is intended for the patient and should be delivered to the patient.

25 Claims, 25 Drawing Sheets

Related U.S. Application Data a continuation-in-part of application No. 12/647,515, filed on Dec. 27, 2009.

(60) Provisional application No. 61/352,140, filed on Jun. 7, 2010, provisional application No. 61/352,155, filed on Jun. 7, 2010, provisional application No. 61/428,944, filed on Dec. 31, 2010, provisional application No. 61/437,796, filed on Jan. 31, 2011.

(51) Int. Cl.
  *A61M 25/00* (2006.01)
  *A61B 50/30* (2016.01)
  *A61B 50/33* (2016.01)
  *A61B 42/00* (2016.01)
  *A61B 46/00* (2016.01)

(52) U.S. Cl.
  CPC ............ *A61B 42/00* (2016.02); *A61B 46/00* (2016.02); *A61B 2050/3008* (2016.02); *A61B 2050/3015* (2016.02); *A61M 25/0017* (2013.01)

(58) Field of Classification Search
  USPC ....... 434/262, 263, 116, 317, 169, 236, 267, 434/269; 705/2; 283/115, 117; 446/295, 446/267, 175, 193, 224, 297, 354, 397, 446/418, 472; 206/571
  See application file for complete search history.

(56) References Cited

U.S. PATENT DOCUMENTS

| | | | | |
|---|---|---|---|---|
| 2,781,611 | A * | 2/1957 | Bills et al. | 446/224 |
| 2,886,316 | A * | 5/1959 | Ayala | 446/267 |
| 2,947,415 | A | 8/1960 | Garth | |
| 2,954,642 | A * | 10/1960 | Jackson | 446/295 |
| 2,959,891 | A * | 11/1960 | Barnett et al. | 446/295 |
| 3,107,786 | A | 10/1963 | Adelman | |
| 3,166,189 | A | 1/1965 | Disston | |
| 3,315,802 | A | 4/1967 | Maro | |
| 3,329,261 | A | 7/1967 | Serany, Jr. et al. | |
| 3,379,339 | A | 4/1968 | Asenbauer | |
| 3,485,352 | A | 12/1969 | Pilger | |
| D218,077 | S | 7/1970 | Gabriel | |
| 3,542,019 | A | 11/1970 | Gittins | |
| 3,726,281 | A | 4/1973 | Norton | |
| 3,851,649 | A | 12/1974 | Villari | |
| D234,404 | S | 2/1975 | Merril | |
| D237,315 | S | 10/1975 | Nowkowski | |
| D237,317 | S | 10/1975 | Nowkowski | |
| 3,967,728 | A | 7/1976 | Gordon et al. | |
| 3,976,195 | A | 8/1976 | Cohen | |
| 3,978,983 | A | 9/1976 | Brezetta | |
| D242,654 | S | 12/1976 | Rawls | |
| 3,998,221 | A | 12/1976 | Collins | |
| D243,798 | S | 3/1977 | Swartz | |
| 4,011,944 | A | 3/1977 | Cooley | |
| 4,053,280 | A | 10/1977 | Salisbury | |
| 4,075,782 | A * | 2/1978 | Neuschatz | 446/295 |
| D248,871 | S | 8/1978 | Forsman et al. | |
| D249,362 | S | 9/1978 | Forsman et al. | |
| 4,160,505 | A | 7/1979 | Rauschenberger | |
| 4,170,300 | A | 10/1979 | Pick | |
| 4,226,328 | A | 10/1980 | Beddow | |
| 4,266,669 | A | 5/1981 | Watson | |
| 4,282,678 | A * | 8/1981 | Tsui | 446/193 |
| 4,307,539 | A * | 12/1981 | Klein | 446/472 |
| D262,995 | S | 2/1982 | Gaba et al. | |
| D268,130 | S | 3/1983 | Easton | |
| 4,458,705 | A | 7/1984 | Cawood | |
| D275,886 | S | 10/1984 | Sheward et al. | |
| D276,462 | S | 11/1984 | Villarreal | |
| D277,508 | S | 2/1985 | Clair | |
| 4,523,679 | A | 6/1985 | Paikoff et al. | |
| 4,530,349 | A * | 7/1985 | Metzger | 128/897 |
| D280,663 | S | 9/1985 | Albon et al. | |
| D280,933 | S | 10/1985 | McLaughlin | |
| D280,993 | S | 10/1985 | McLaughlin | |
| D283,051 | S | 3/1986 | Fichera | |
| D287,760 | S | 1/1987 | Discko, Jr. | |
| 4,761,008 | A | 8/1988 | Huggins | |
| 4,767,008 | A | 8/1988 | Warnecke et al. | |
| 4,795,441 | A | 1/1989 | Bhatt | |
| 4,828,113 | A | 5/1989 | Friedland | |
| 4,844,259 | A | 7/1989 | Glowczewskie et al. | |
| 4,858,821 | A | 8/1989 | Bickelhaupt | |
| D310,896 | S | 9/1990 | Winjum | |
| 4,991,877 | A | 2/1991 | Lieberman | |
| 5,007,535 | A | 4/1991 | Meseke et al. | |
| 5,024,326 | A | 6/1991 | Sandel et al. | |
| 5,031,768 | A | 7/1991 | Fischer | |
| 5,094,621 | A * | 3/1992 | Friedel | 434/236 |
| 5,163,557 | A | 11/1992 | Sokolowski | |
| 5,170,804 | A | 12/1992 | Glassman | |
| 5,197,885 | A * | 3/1993 | Friedel | 434/236 |
| D334,973 | S | 4/1993 | Valentine et al. | |
| D337,830 | S | 7/1993 | Coyne et al. | |
| 5,232,369 | A * | 8/1993 | Mavrikis | 434/262 |
| 5,244,394 | A * | 9/1993 | Serabian-Musto | 434/263 |
| D343,687 | S | 1/1994 | Houghton et al. | |
| 5,312,287 | A * | 5/1994 | Chuang | 446/295 |
| 5,314,339 | A * | 5/1994 | Aponte | 434/267 |
| 5,318,543 | A | 6/1994 | Ross et al. | |
| 5,324,201 | A * | 6/1994 | Friedel | 434/236 |
| 5,339,955 | A | 8/1994 | Horan et al. | |
| D351,661 | S | 10/1994 | Fischer | |
| 5,392,918 | A | 2/1995 | Harrison | |
| 5,411,437 | A * | 5/1995 | Weber et al. | 434/269 |
| 5,487,566 | A | 1/1996 | Hedge, Jr. | |
| D380,272 | S | 6/1997 | Partika et al. | |
| 5,665,945 | A * | 9/1997 | Oshima | 200/1 R |
| D387,177 | S | 12/1997 | Davis | |
| D387,559 | S | 12/1997 | Williamson | |
| 5,713,778 | A * | 2/1998 | Radosevich et al. | 446/304 |
| 5,720,502 | A * | 2/1998 | Cain | 283/115 |
| 5,778,574 | A | 7/1998 | Reuben | |
| 5,779,053 | A | 7/1998 | Partika | |
| 5,795,213 | A * | 8/1998 | Goodwin | 446/297 |
| 5,820,441 | A * | 10/1998 | Pracas | 446/354 |
| 5,827,262 | A | 10/1998 | Neftel | |
| 5,829,790 | A | 11/1998 | Phillips | |
| 5,941,241 | A | 8/1999 | Weinstein et al. | |
| 5,947,284 | A | 9/1999 | Foster | |
| 5,954,369 | A | 9/1999 | Seabrook | |
| 5,975,295 | A | 11/1999 | Diamond | |
| 6,004,136 | A * | 12/1999 | Ehrenpreis | 434/262 |
| 6,012,586 | A | 1/2000 | Misra | |
| 6,068,121 | A | 5/2000 | McGlinch | |
| 6,089,943 | A * | 7/2000 | Lo | 446/175 |
| 6,142,152 | A | 11/2000 | Gawarecki | |
| 6,158,437 | A | 12/2000 | Vagley | |
| 6,159,017 | A * | 12/2000 | Coomansingh | 434/267 |
| D442,697 | S | 5/2001 | Hajianpour | |
| D450,130 | S | 11/2001 | Goldstein | |
| D450,391 | S | 11/2001 | Hunt et al. | |
| 6,330,427 | B1 * | 12/2001 | Tabachnik | 434/317 |
| 6,361,396 | B1 * | 3/2002 | Snyder et al. | 446/397 |
| 6,382,212 | B1 | 5/2002 | Borchard | |
| 6,405,863 | B1 | 6/2002 | Dhindsa | |
| 6,454,097 | B1 | 9/2002 | Blanco | |
| 6,579,271 | B1 | 6/2003 | Aruffo et al. | |
| 6,659,506 | B1 | 12/2003 | Erisalu | |
| 6,681,933 | B1 | 1/2004 | Demsien et al. | |
| 6,769,546 | B2 | 8/2004 | Busch | |
| D495,491 | S | 9/2004 | Ramirez | |
| 6,793,078 | B2 | 9/2004 | Roshdy | |
| 6,840,379 | B2 | 1/2005 | Franks-Farah et al. | |
| 6,896,141 | B2 | 5/2005 | McMichael et al. | |
| 6,915,901 | B2 | 7/2005 | Feinberg | |
| 6,926,708 | B1 | 8/2005 | Franks-Farah et al. | |
| 6,948,742 | B2 | 9/2005 | Buck | |
| 7,048,120 | B2 | 5/2006 | Pond | |

(56) References Cited

U.S. PATENT DOCUMENTS

| | | | |
|---|---|---|---|
| 7,066,328 B2 | 6/2006 | Pulsifer | |
| D530,920 S | 10/2006 | Snell | |
| D547,064 S | 7/2007 | Snell | |
| D549,454 S | 8/2007 | Åhman | |
| 7,264,869 B2 | 9/2007 | Tobita | |
| 7,278,987 B2 | 10/2007 | Solazzo | |
| D557,047 S | 12/2007 | Dretzka | |
| D561,473 S | 2/2008 | Phillips et al. | |
| D563,673 S | 3/2008 | Dretzka | |
| 7,401,703 B2 | 7/2008 | McMichael | |
| 7,434,687 B2 | 10/2008 | Itou et al. | |
| D579,662 S | 11/2008 | Dretzka | |
| D590,596 S | 4/2009 | Dretzka | |
| D596,311 S | 7/2009 | Antons | |
| 7,624,869 B2 | 12/2009 | Primer | |
| D609,819 S | 2/2010 | Tomes et al. | |
| D612,153 S | 3/2010 | Liao | |
| 7,785,312 B2 | 8/2010 | Thorne | |
| D638,137 S | 5/2011 | Gross et al. | |
| D662,218 S | 6/2012 | Pittman | |
| 8,448,786 B2 | 5/2013 | Tomes et al. | |
| D688,461 S | 8/2013 | Ambrefe et al. | |
| 8,628,549 B2 | 1/2014 | To et al. | |
| 8,631,935 B2 | 1/2014 | Tomes et al. | |
| 8,678,190 B2 | 3/2014 | Tomes et al. | |
| 8,708,999 B2 | 4/2014 | Hong et al. | |
| D708,347 S | 7/2014 | Lober | |
| D708,759 S | 7/2014 | Heyman et al. | |
| D720,470 S | 12/2014 | Lober | |
| D720,471 S | 12/2014 | Angel et al. | |
| 9,283,352 B2 | 3/2016 | Tomes et al. | |
| 9,522,753 B2 | 12/2016 | Tomes et al. | |
| 2002/0185406 A1 | 12/2002 | Massengale | |
| 2003/0031995 A1* | 2/2003 | Laura | 434/317 |
| 2003/0038475 A1* | 2/2003 | Stancil | 283/117 |
| 2003/0075474 A1 | 4/2003 | Moyer et al. | |
| 2003/0159969 A1 | 8/2003 | McMichael et al. | |
| 2004/0004019 A1 | 1/2004 | Busch | |
| 2004/0161732 A1* | 8/2004 | Stump et al. | 434/262 |
| 2004/0180822 A1 | 9/2004 | Grafton | |
| 2004/0195145 A1 | 10/2004 | Roshdy | |
| 2004/0238391 A1 | 12/2004 | Pond | |
| 2005/0022822 A1 | 2/2005 | Santilli | |
| 2005/0101905 A1 | 5/2005 | Merry | |
| 2005/0228691 A1* | 10/2005 | Paparo | 705/2 |
| 2005/0256453 A1 | 11/2005 | Nagamatsu | |
| 2005/0285385 A1 | 12/2005 | Bova | |
| 2006/0009742 A1* | 1/2006 | Solazzo | A61B 90/11 604/356 |
| 2006/0029912 A1* | 2/2006 | Kearby et al. | 434/116 |
| 2006/0088355 A1* | 4/2006 | Ribi | 400/88 |
| 2006/0186010 A1 | 8/2006 | Warnack | |
| 2006/0264822 A1 | 11/2006 | Nagamatsu | |
| 2006/0271019 A1* | 11/2006 | Stoller | A61F 5/44 604/544 |
| 2007/0026472 A1 | 2/2007 | Prokash et al. | |
| 2007/0060908 A1 | 3/2007 | Webster et al. | |
| 2007/0065792 A1* | 3/2007 | Schubarth | 434/263 |
| 2007/0084742 A1 | 4/2007 | Miller et al. | |
| 2007/0088330 A1 | 4/2007 | House | |
| 2007/0095699 A1 | 5/2007 | Frieze | |
| 2007/0142786 A1 | 6/2007 | Lampropoulos | |
| 2007/0161971 A1 | 7/2007 | House | |
| 2007/0225687 A1 | 9/2007 | House | |
| 2007/0299431 A1 | 12/2007 | Jakubowski et al. | |
| 2008/0116106 A1 | 5/2008 | Lampropoulos et al. | |
| 2008/0121553 A1 | 5/2008 | Gobel | |
| 2008/0221515 A1 | 9/2008 | Nagamatsu | |
| 2008/0283426 A1 | 11/2008 | Primer et al. | |
| 2008/0283433 A1* | 11/2008 | Primer | 206/440 |
| 2009/0071854 A1 | 3/2009 | Martin | |
| 2009/0152160 A1 | 6/2009 | Thompson et al. | |
| 2009/0184026 A1 | 7/2009 | Massengale et al. | |
| 2009/0194453 A1 | 8/2009 | Thorne et al. | |
| 2009/0234346 A1 | 9/2009 | McBride et al. | |
| 2009/0236259 A1 | 9/2009 | Hicks | |
| 2010/0274205 A1 | 10/2010 | Morelli et al. | |
| 2010/0307942 A1 | 12/2010 | Tomes et al. | |
| 2010/0311026 A1 | 12/2010 | Tomes et al. | |
| 2011/0107494 A1 | 5/2011 | Haines | |
| 2011/0155599 A1 | 6/2011 | Yakel et al. | |
| 2011/0297147 A1 | 12/2011 | Lick et al. | |

FOREIGN PATENT DOCUMENTS

| | | |
|---|---|---|
| JP | 2007-229520 | 9/2007 |
| WO | WO-99/26857 | 6/1999 |
| WO | WO-2005/027767 | 3/2005 |
| WO | WO-2006/114466 | 11/2006 |
| WO | WO-2007/045943 | 4/2007 |

OTHER PUBLICATIONS

Dictionary definition m-w. URL: <http://www.merriam-webster.com/dictionary/reassure>. Retrieved from Internet Dec. 10, 2013.*

Lion King Stickers website. URL: <http://tlkobsession.wuffpaws.org/OldSite/games/games2.html>. 1996. Retrieved from Internet Dec. 10, 2013.*

Lion Sticker Activity Book website. URL: <http://www.amazon.com/Disneys-Simbas-Pride-Sticker-Activity/dp/B0018DOJZA>. 1998. Retrieved from Internet Dec. 10, 2013.*

Naming a character website. URL: <https://web.archive.org/web/20080410122058/http://www.wikihow.com/Make-Your-Own-Anime-or-Manga-Character>. 2008. Retrieved from Internet Dec. 10, 2013.*

Naming Characters on Cards website. URL:<https://web.archive.org/web/20060219171403/http://www.hubbardscupboard.org/brown_bear_brown_bear.html>. (2006).. Retrieved from Internet Dec. 11, 2013.*

Poon, Robert "Non-Final Office Action", U.S. Appl. No. 12/495,148, filed Jun. 30, 2009; first inventor: Jennifer E. Tomes; dated Aug. 4, 2010.

Yuan, Minqiang "Non-Final Office Action", Chinese Application No. 200920267201.2, dated Sep. 9, 2010.

European Patent Office, "Extended EPO Search Report", EPO Application No. 10251025.2, in the Name of Medline Industries, dated Sep. 29, 2010.

Medline, "Medline Aritcle/Brochure", Published 2008.

Yuan, Minqiang "Non-Final Office Action", Chinese Application No. 200920267201.2, dated Jun. 4, 2010.

European Patent Office, "Extended EPO Search Report", Application No. 10251024.5, in the Name of Medline Industries, dated Oct. 18, 2010.

Examiner, Chinese Patent Office "First Office Action", dated Nov. 18, 2010 application 201020219785.9 filed Jun. 3, 2010.

Poon, Robert "Final Office Action", U.S. Appl. No. 12/495,148, filed Jun. 30, 2009, dated Mar. 3, 2011.

Prange, Sharon M., "Response to First Office Action", dated Aug. 6, 2009 U.S. Appl. No. 12/004,796 Inventor: Jonathan S. Primer et al. filed Dec. 21, 2007.

Cavanna, Mark "Notice of Allowance", U.S. Appl. No. 29/362,279, filed May 21, 2010, dated Sep. 19, 2011.

Byun, Sung C., "PCT Search Report", PCT/US2011/068193; filed Dec. 30, 2011; dated Aug. 22, 2012.

Poon, Robert "Restriction Requirement", U.S. Appl. No. 12/647,515, filed Dec. 27, 2009; dated May 23, 2012.

Cavanna, Mark "Ex Parte Quayle Action", U.S. Appl. No. 29/380,474, filed Dec. 6, 2010; dated Aug. 14, 2012.

Poon, Robert "NonFinal Office Action", U.S. Appl. No. 12/647,515, filed Dec. 27, 2009; dated Jun. 28, 2012.

Poon, Robert "NonFinal OA", U.S. Appl. No. 12/495,148, filed Jun. 30, 2009; dated Oct. 4, 2012.

Poon, Robert "NonFinal Office Action", U.S. Appl. No. 13/153,300, filed Jun. 3, 2011; dated Oct. 1, 2012.

Poon, Robert "NonFinal Office Action", U.S. Appl. No. 13/374,509, filed Dec. 30, 2011; dated Oct. 2, 2012.

Poon, Robert "Final Office Action", U.S. Appl. No. 12/846,675, filed Jul. 29, 2010; dated Sep. 26, 2012.

(56) References Cited

OTHER PUBLICATIONS

Byun, Sung C., "PCT Search Report", PCT/US2012/039311; Filed May 24, 2011; dated Oct. 25, 2012.
"EPO Intent to Grant", EPO Application No. 10251024.5; Filed Jun. 2, 2010; dated Nov. 2, 2012.
Byun, Sung Cheal "PCT Search Report and Written Opinion", PCT/US2012/037524; Filed May 11, 2012; dated Nov. 16, 2012.
Hand, Melanie J., "NonFinal OA", U.S. Appl. No. 13/155,026, filed Jun. 7, 2011; dated Nov. 30, 2012.
Poon, Robert "NonFinal Office Action", U.S. Appl. No. 12/846,675, filed Jul. 29, 2010; dated Dec. 22, 2011.
Cavanna, Mark "NonFinal Office Action", U.S. Appl. No. 29/380,474, filed Dec. 26, 2012; dated Mar. 27, 2012.
Cavanna, Mark "Notice of Allowance", U.S. Appl. No. 29/338,022, filed Jun. 3, 2009; dated Oct. 1, 2009.
Hand, Melanie J., "NonFinal OA", U.S. Appl. No. 12/785,064, filed May 21, 2010; dated Feb. 1, 2013.
Hand, Melanie J., "Notice of Allowance", U.S. Appl. No. 13/155,026, filed Jun. 7, 2011; dated Feb. 1, 2013.
Hand, Melanie J., "NonFinal OA", U.S. Appl. No. 13/115,053, filed Jun. 7, 2011; dated May 9, 2013.
Poon, Robert "Final OA", U.S. Appl. No. 12/647,515, filed Dec. 27, 2009; dated May 13, 2013.
Hand, Melanie J., "Final OA", U.S. Appl. No. 12/785,064, filed May 21, 2010; dated Jun. 5, 2013.
Poon, Robert "Final Office Action", U.S. Appl. No. 12/495,148, filed Jun. 30, 2009; dated Jul. 31, 2013.
Poon, Robert "Final OA", U.S. Appl. No. 13/374,509, filed Dec. 30, 2011; dated Aug. 6, 2013.
Poon, Robert "Final OA", U.S. Appl. No. 13/153,300, filed Jun. 3, 2011; dated Aug. 6, 2013.
Poon, Robert "NonFinal Office Action", U.S. Appl. No. 12/846,675, filed Jul. 29, 2010; dated Sep. 10, 2013.
Cavanna, Mark "Notice of Allowance", U.S. Appl. No. 29/444,526, filed Jan. 31, 2013; dated Oct. 17, 2013.
Hand, Melanie J., "Notice of Allowance", U.S. Appl. No. 13/155,054, filed Jun. 7, 2011; dated Oct. 28, 2013.
Poon, Robert "Notice of Allowance", U.S. Appl. No. 12/495,148, filed Jun. 30, 2009; dated Nov. 20, 2013.
Poon, Robert "NonFinal OA", U.S. Appl. No. 12/647,515, filed Dec. 27, 2009; dated Dec. 18, 2013.
Poon, Robert "Final OA", U.S. Appl. No. 12/846,675, filed Jul. 29, 2010; dated Dec. 18, 2013.
"Extended EPO Exam Report", EPO App No. 10251025.2; Filed Jun. 2, 2010; dated Dec. 17, 2013.
Poon, Robert "Notice of Allowance", U.S. Appl. No. 12/846,675, filed Jul. 29, 2010, dated Apr. 30, 2014.
Gimenez Burgos, R "Extended European Search Report", 11854003.8; Filed Dec. 30, 2011; dated Jun. 3, 2014.
"Bardex I.C. Infection Control Foley Tray", *Bard Infection Control System; Bardex I.C. Directions for Use Infection Control Foley Tray*; Copyright Dated 2006.
"Bardex I.C. Complete Care StateLock Device 350 ml Urine Meter Foley Tray with Bacteriostatic Collection System", *Bard Infection Control System; Bardex I.C. Complete Care Directions for Use*; Copyright Dated Sep. 2006.
"Bardex I.C. Infection Control 350ml Urine Meter Foley Tray", *Bard Infection Control System; Bardex I.C. Urine Meter Foley Tray Directions for Use*; Copyright Dated 2006.
"Bard Medical Division Care & Catheterization Script", *Care & Catheterization/Preventing UTI Script for education video; Preventing UTI: Care and Catheterization Techniques*; Copyright 2006; AV0512-06 R12/05 XXX.
Medline Industries, Inc. vs C.R. Bard, Inc; No. 14-cv-3618; C.R. Bard's LPR 2.3 Contentions—Initial Non-Infringement; Exhibits 1 and A-H; Dated Sep. 5, 2014.
Medline Industries, Inc. vs C.R. Bard, Inc; No. 1:14-cv-03618; Medline Industries, Inc.'s Response to C.R. Bard's Initial Invalidity Contentions; Exhibits A-H; Dated Sep. 19, 2014.
Medline Industries, Inc. vs C.R. Bard, Inc; No. 1:14-cv-3618; Responses to Medline Industries, Inc.'s First set of Requests for the Production of Documents; Dated Sep. 26, 2014.
Medline Industries, Inc. vs C.R. Bard, Inc; No. 1:14-cv-03618; Response to Medline Industries, Inc.'s First Set of Interrogatories; Dated Sep. 26, 2014.
"Publication", European Commission: Pharmaceutical Committee "*A Guideline on the Readability of the Label and Package Leaflet of Medicinal Products for Human Use*"; Dated Sep. 29, 1998.
"Bard Publication", "*A few important words about Catheter Care*"; C.R. Bard, Inc; Copyright 2001 C.R. Bard, Inc.
*Dover Intermittent Catheter Tray—14 fr, Red Rubber*; Website http://tinyurl.com/o4esrwh; Unknown Publication Date.
"NonFinal Office Action", U.S. Appl. No. 13/680,902, filed Apr. 11, 2014; dated Dec. 2, 2014.
"Inter Partes Review Petition for U.S. Pat. No. 8,448,786", U.S. Pat. No. 8,448,786; filed Dec. 30, 2014; Mailed Dec. 30, 2014.
"Inter Partes Review Petition", IPR Exhibit—Kimmel Declaration U.S. Pat. No. 8,448,786; Dr. Robert M. Kimmel Declaration; Received Dec. 30, 2014.
"Inter Partes Review Petition", Exhibit; Kimmel CV—Dr. Robert M. Kimmel; Mailed Dec. 30, 2014.
"Inter Partes Review Petition", IPR Exhibit—Susan Carrow Declaration U.S. Pat. No. 8,448,786; mailed Dec. 30, 2014.
"Inter Partes Review Petition", Exhibit; Carrow CV—Susan Carrow CV; Mailed Dec. 30, 2014.
"Inter Partes Review Petition", Exhibit; *EC Guideline 2009; "Guideline on the Readability of the Labelling and Package Leaflet of Medicinal Products for Human Use*"; Revision 1 Published Jan. 12, 2009 (Jan. 12, 2009); Mailed Dec. 30, 2014.
"Inter Partes Review Petition", Exhibit—*EC Guideline 1998; "A Guideline on the Readability of the Label and Package Leaflet of Medicinal Products for Human Use*"; Published Sep. 29, 1998; Mailed Dec. 30, 2014.
"Inter Partes Review Petition", Exhibit—Soroka Glossary_wrap; *Illustrated Glossary of Packaging Terminology*; second edition; publication date unknown.
"Inter Partes Review Petition", Exhibit—Soroka Glossary 'Bag'; *Illustrated Glossary of Packaging Terminology*, second edition; Walter Soroka; publication unknown.
"Inter Partes Review Petition", Exhibit—*Encyclopedia Dictionary of Medicine, Nursing and Allied Health*; Miller Keane, Seventh Edition.
"Inter Partes Review Petition", Exhibit—*Dorland's Definition of Bag; Dorland's Illustrated Medical Dictionary*; 31st Edition; Publication Date Unknown.
"Inter Partes Review Petition", Exhibit—*Nursing Standard; Article in Learning Zone—Continue Professional Development; "Reducing the risks associated with urinary catheters*"; Published Mar. 25, 2009.
"Inter Partes Review Petition", Exhibit—*Websters Dictionary Definition of Dispose; Webster's Third New International Dictionary*; Copyright 2003; publication date unknown.
"Inter Partes Review Petition", Exhibit—*Bard DFU; Bardex Infection Control Foley Tray*; Copyright 2006, publication date unknown.
"Inter Partes Review Petition", Exhibit—Medline Initial Infringement Contentions; Medline Industries vs. C.R. Bard; dated Aug. 22, 2014.
"Inter Partes Review Petition", Exhibit—*FDA Article; Guidance for the Content of Premarkt Notifications fro Conventional and Antimicrobial Foley Catheters*; http://www.fda.gov/medicaldevices/deviceregulationandguidance/guidancedocuments/ucm080884.htm; Unknown Publication Date.
"Inter Partes Review Petition", Exhibit—*Bardex DFU; Directions for Use/Patient Education Information—Urology*; Unknown Publication Date.
"Inter Partes Review Petition", Exhibit—*Mosby's Pocket Guide Excerpt; Mosby's Pocket Guide to Basic Skills and Procedures*; Sixth Edition; Perry & Potter; "*Urinary Catheter: Indwelling, Straight, Care and Removal*"; Unknown Publication Date.
"Inter Partes Review Petition", Exhibit—*Health Protection Scotland; CAUTI Maintenance Bundel*; Version 2, Feb. 2008.

(56) References Cited

OTHER PUBLICATIONS

"Inter Partes Review Petition", Exhibit—*FAQs "Catheter-Associated Urinary Tract Infection"*; Unknown Publisher; Unknown Publication Date.
"Inter Partes Review Petition for U.S. Pat. No. 8,631,935", Inter Partes Review Petition for U.S. Pat. No. 8,631,935 for claims 1-4 and 11-20; Filed Dec. 30, 2014.
"Inter Partes Review Petition for U.S. Pat. No. 8,631,935", Inter Partes Review Petition for U.S. Pat. No. 8,631,935 for Claims 7-8, 10, 21-23, 25, 27-28, and 30-34; Filed Dec. 30, 2014.
"Inter Partes Review Petition for U.S. Pat. No. 8,678,190", Inter Partes Review Petition for U.S. Pat. No. 8,678,190; Filed Dec. 30, 2014.
"Inter Partes Review Petition", Exhibit—Response to Office Action in U.S. Appl. No. 12/495,148, filed Jun. 30, 2009; Response Filed Nov. 19, 2010.
"Inter Partes Review Petition", Exhibit—RCE Filed Nov. May 31, 2011 for U.S. Appl. No. 12/495,148, filed Jun. 30, 2009.
"Inter Partes Review Petition", Exhibit—Amendment filed on Apr. 3, 2013 for U.S. Appl. No. 12/495,148, filed Jun. 30, 2009.
"Inter Partes Review Petition", Exhibit—*Infection Control Today Article; Medical Center Cuts Catheterizations by 21 Percent with Foley Catheter Management System*; Published 2010.
"Inter Partes Review Petition", Exhibit—*Morning Start Article; "Floyd Medical Center Reduces Catheter-Associated Urinary Tract Infections 83 Percent and Catheter Use by 23 Percent"*; Published Jan. 2011.
"Inter Partes Review Petition", Exhibit—*Medical News Today Article; 'Getting to Zero:' Medlines' Erase Cauti Program Helps Hospitals Reduce Catheter Use by 20 Percent*; Article Date Apr. 13, 2011.
"Inter Partes Review Petition", Exhibit—*The Journal of Healthcare Contracting*, Oct. 2012; "*Catheter-associated urinary tract infections*".
"Inter Partes Review Petition", IPR Exhibit—Kimmel Declaration for U.S. Pat. No. 8,631,935 claims 1-4 and 11-20; Declaration of Dr. Robert M. Kimmel; Mailed Dec. 30, 2014.
"Inter Partes Review Petition", IPR Exhibit—Carrow Declaration for U.S. Pat. No. 8,631,935 claims 1-4 and 11-20; Susan Carrow Declaration; Mailed Dec. 30, 2014.
"Inter Partes Review Petition", IPR Exhibit—Kimmel Declaration for U.S. Pat. No. 8,631,935 claims 7-8, 10, 21-23, 25, 27-28, and 30-34; Declaration of Dr. Robert M. Kimmel; Mailed Dec. 30, 2014.
"Inter Partes Review Petition", IPR Exhibit—Kimmel Declaration for U.S. Pat. No. 8,768,190; Declaration of Dr. Robert M. Kimmel; Mailed Dec. 30, 2014.
"Inter Partes Review Petition", IPR Exhibit—Carrow Declaration for U.S. Pat. No. 8,768,190; Declaration of Susan Carrow; Mailed Dec. 30, 2014.
Poon, Robert "NonFinal OA", U.S. Appl. No. 14/265,909, filed Apr. 30, 2014; dated Dec. 31, 2014.
Poon, Robert "NonFinal OA", U.S. Appl. No. 14/265,920, filed Apr. 30, 2014; dated Dec. 30, 2014.
Gimenez Burgos, R "European Examination Report", European Application No. 11 854 003.8-1659; dated Jan. 22, 2015.
Gimenez Burgos, R "Extended European Search Report", EPO App No. 12 79 3939; dated Jan. 27, 2015.
Gimenez Burgos, R "Extended European Search Report", EU App No. 12792423.1-1659/2713933; PCT/US2012039311; dated Jan. 27, 2015.
"Bard IPR Exhibit", "Inter Partes Review Petition", IPR Exhibit—Carrow Declaration for U.S. Pat. No. 8,631,935; Susan Carrow Declaration; Mailed Dec. 30, 2014.
"Article 94(3) EPC Examination", European Application No. 10 251 025.2-1501; dated Mar. 13, 2015.
Poon, Robert "Final OA", U.S. Appl. No. 12/647,515, filed Dec. 27, 2009; dated Apr. 7, 2015.
"Office Action", Chinese Application No. 201180066491.4; dated Mar. 24, 2015.

"Inter Partes Review—Patent Owner Response", Inter Partes Review—Patent Owner Response; U.S. Pat. No. 8,448,786; Filed Apr. 22, 2015.
"Inter Partes Review—Patent Owner Response", Inter Partes Review—Patent Owner Response; U.S. Pat. No. 8,631,935; Inter Partes Review No. IPR2015-00511; Filed Apr. 22, 2015.
"Inter Partes Review—Patent Owner Response", Inter Partes Review—Patent Owner Response; Patent 8,631,935; Inter Partes Review No. IPR2015-00513; Filed Apr. 21, 2015.
"Inter Partes Review—Patent Owner Response", Inter Partes Review—Patent Owner Response; U.S. Pat. No. 8,678,190; Inter Partes Review No. IPR2015-00514; Filed Apr. 21, 2015.
"IPR2015-00514 Decision Institution of Inter Partes Review" IPR2015-00514; U.S. Pat. No. 8,678,190; Mailed Jun. 26, 2015; Decision Institution of Inter Partes Review.
"IPR2015-00509 Institution Decision", IPR2015-00509; U.S. Pat. No. 8,448,786; Mailed Jul. 15, 2015; Decision Denying Institution of Inter Partes Review.
"IPR 2015-00514 Petitioner's Request for Rehearing", IPR 2015-00514 Petitioner's Request for Rehearing; U.S. Pat. No. 8,678,190; Dated Jul. 10, 2015.
"IPR2015-00511 Institution Decision", IPR2015-00511; U.S. Pat. No. 8,631,935; Entered Jul. 15, 2015; Decision Denying Institution of Inter Partes Review.
"IPR2015-00513 Institution Decision", IPR2015-00513 Institution Decision; U.S. Pat. No. 8,631,935; Entered Jul. 15, 2015; Decision Institution of Inter Partes Review.
Hand, Melanie Jo "Final OA", U.S. Appl. No. 13/860,902, filed Apr. 11, 2013; dated May 22, 2015.
"IPR 2015-00514—Request for Rehearing Denied", IPR2015-00514; U.S. Pat. No. 8,678,190; Decision on Request for Rehearing—Denied; Mailed Jul. 16, 2015.
"IPR 2015-00514—Patent Owner's Objection to Evidence", IPR 2015-00514—Patent Owner's Objection to Evidence Submitted During a Preliminary Proceeding; U.S. Pat. No. 8,678,190; Mailed Jul. 13, 2015.
"IPR2015-00513—Patent Owner's Request for Adverse Judgement", U.S. Pat. No. 8,631,935; Mailed Jul. 23, 2015.
"IPR0215-00513 Scheduling Order", U.S. Pat. No. 8,631,935; Mailed Jul. 15, 2015.
"IPR 2015-00514—Patent Owner's Request for Adverse Judgement", U.S. Pat. No. 8,678,190; Mailed Jul. 23, 2015.
"IPR2015-00514—Scheduling Order", U.S. Pat. No. 8,678,190; Mailed Jun. 26, 2015.
"IPR2015-00514 Judgement—Termination of Proceeding" U.S. Pat. No. 8,678,190; Mailed Jul. 24, 2015.
Hand, Melanie J., "Notice of Allowance", U.S. Appl. No. 13/860,902, filed Apr. 11, 2013; dated Aug. 4, 2015.
"IPR2015-00513—Request for Adverse Judgement", IPR2015-00513—Request for Adverse Judgement; Granted—Proceedings Terminated; U.S. Pat. No. 8,631,935; Entered Aug. 11, 2015.
"Australian First Exam Report", AU Patent Application No. 2011351971; Patent Examination Report No. 1; dated Jul. 25, 2015.
Poon, Robert "Final OA", U.S. Appl. No. 14/265,920, filed Apr. 30, 2014; dated Oct. 2, 2015.
Poon, Robert "Final OA", U.S. Appl. No. 14/265,909, filed Apr. 30, 2015; dated Oct. 5, 2015.
*Medline Industries, Inc.* vs *C.R. Bard, Inc*; No. 1:14-cv-03618; Notice of Medline Industries Inc's Motion to Dismiss C.R. Bard Inc's Inequitable Conduct Counterclaim and to strike affirmative defense for the '786 Patent; Filed Oct. 20, 2015.
*Medline Industries, Inc.* vs *C.R. Bard, Inc*; No. 1:14-cv-03618; Medline Industries Inc's Opposition to C.R.Bard Inc's Motion for Leave to File Second Amended Answer to Add Counterclaim; Filed Oct. 20, 2015.
Chinese Application No. 201280035240.4; Filed May 24, 2012; dated Aug. 18, 2015.
Hand, Melanie J., "NonFinal OA", U.S. Appl. No. 14/165,044, filed Jan. 27, 2014; dated Oct. 26, 2015.
Poon, Robert "NonFinal OA", U.S. Appl. No. 14/718,792, filed May 21, 2015; dated Nov. 19, 2015.
*Medline Industries* vs. *CR Bard, Inc*; No. 14-cv-3618; C.R. Bard's LPR 3.1 Contentions; Filed Nov. 24, 2015.

(56) References Cited

OTHER PUBLICATIONS

"Office Action Received", Chinese App No. 201280035246.1; NonFinal OA; dated Sep. 16, 2015.
Poon, Robert "Final Office Action", U.S. Appl. No. 14/718,912, filed May 21, 2015, dated Jan. 5, 2016.
"Office Action", Chinese Application No. 201180066491.4; dated Nov. 11, 2015.
"Office Action", Chinese Application No. 201180066491.4; dated Nov. 11, 2015.
Poon, Robert "Notice of Allowance", U.S. Appl. No. 14/718,792, filed May 21, 2015; dated Feb. 2, 2016.
"Office Action", Australian Application No. 2011351971; dated Feb. 18, 2016.
Notice of Allowance; EP Application No. 10251025.2-1501; dated Feb. 18, 2016.
Mackenzie, Kristian "Office Action", Canadian Application No. 2,705,670; dated Apr. 25, 2016.
Mackenzie, Kristian "Office Action", Canadian Application No. 2,705,647; dated Apr. 21, 2016.
Hand, Melanie Jo "Appeal Decision", U.S. Appl. No. 12/785,064, filed May 21, 2010; dated May 18, 2016.
Poon, Robert "NonFinal OA", U.S. Appl. No. 15/067,903, filed Mar. 11, 2016; dated Jun. 30, 2016.
"Second Office Action", Chinese Application No. 201280035240.4; dated Jun. 23, 2016.
"Intent to Grant", Chinese Application No. 201180066491.4; Flled Dec. 30, 2011; dated Jul. 6, 2016.
"Notice of Acceptance", Australian Application No. 2011351971; Filed Dec. 30, 2011; dated May 13, 2016.
"Office Action", Chinese Application No. 201280035246.1; Filed May 11, 2012; dated Jul. 15, 2016.
Marcetich, Adam M., "Final OA", U.S. Appl. No. 14/165,044, filed Jan. 27, 2014; dated Aug. 11, 2016.
*Medline Industries Inc.* vs *C.R. Bard, Inc*; C.R. Bard's LPR 3.1 Contentions; Civil Action No. 1:16-cs-3529; Judge Sharon Johnson Coleman; Filed Aug. 26, 2016.
"Medline Catalog", *Turkel Safety Thoracentesis Procedure Trays by Covidien*; http://www.medline.com/jump/sku/x/MDPKDL566059; Unknown Publication date but believed to be prior to present application filing date.
"Medline Catalog", *Turkel Safety Thoracentesis Procedure Trays by Covidien*; 5; http://www.medline.com/sku/item/MDPKDL566075; Unknown Publication date but believed to be prior to present application filing date.
"Medline Catalog", *Paracentesis Trays by Covidien*; http://www.medline.com/sku/item/MDPSWD568006; Unknown Publication Date but believed to be prior to filing of present application.
"Medline Catalog", *Argyle Turkel Safety Thoracentesis System by Covidien*; http://www.medline.com/sku/item/MDPKDL5014; Unknown Publication Date but believe to be prior to filing of present application.
"Medline Catalog", *Argyle Trocar Catheter Kits by Covidien*; http://www.medline.com/sku/item/MDPSWD565028; Unknown Publication Date but believed to be prior to filing of present application.
"Medline Catalog", *Paracentesis Trays by Halyard Health*; http://www.medline.com/sku/item/MDPBAA61450; Unknown Publication Date but believed to be prior to filing of present application.
"Medline Catalog", *Safe-T Thoracentesis/Paracentesis Tray by Carefusion*; http://www.medline.com/sku/item/ MDPBXTTPT1000SP; Unknown publication date but believed to be prior to filing of present application.
"Medline Catalog", *Thoracentesis Trays by Carefusion*; http://www.medline.com/sku/item/MDPBXTPIG1280K; Unknown publication date but believed to be prior to filing of present application.
"Medline Catalog", *Argyle Turkel Safety Thoracentesis System by Covidien*; 6; http://www.medline.com/sku/item/MDPKDL5016; Unknown Publication Date but believed to be prior to filing of present application.
Hand, Melanie Jo "Non-Final OA", U.S. Appl. No. 13/860,902, filed Apr. 11, 2013; dated Apr. 1, 2016.
Marcetich, Adam "Notice of Allowance", U.S. Appl. No. 13/860,902, filed Apr. 11, 2013; dated Sep. 14, 2016.
Poon, Robert "NonFinal OA", U.S. Appl. No. 14/265,909, filed Apr. 30, 2014; dated Sep. 12, 2016.
Vasat, Peter "Notice of Allowance", U.S. Appl. No. 12/785,064, filed May 21, 2010; dated Sep. 12, 2016.
Cavanna, Mark "Non-Final Office Action", U.S. Appl. No. 29/479,600, filed Jan. 17, 2014; dated Sep. 26, 2016.
Poon, Robert "Appeal Decision", U.S. Appl. No. 13/374,509, filed Dec. 30, 2011; dated Oct. 24, 2016.
Poon, Robert "Appeal Decision", U.S. Appl. No. 13/153,300, filed Jun. 3, 2011; dated Oct. 12, 2016.
Marcetich, Adam "Notice of Allowance", U.S. Appl. No. 13/860,902, filed Apr. 11, 2013; dated Nov. 8, 2016.
Schultz, Ottmar "Extended European Search Report" EP Application No. 16177903.8-1501; Filed Jun. 30, 2009; dated Oct. 27, 2016.
"Office Action", Chinese Application No. 201280035246.1; Filed May 11, 2012; dated Nov. 28, 2016.
Poon, Robert "Final OA", U.S. Appl. No. 15/067,903, filed Mar. 11, 2016; dated Jan. 13, 2017.
Poon, Robert "Final OA", U.S. Appl. No. 14/265,909, filed Apr. 30, 2014; dated Jan. 10, 2017.
Marcetich, Adam "Notice of Allowance", U.S. Appl. No. 14/165,044, filed Jan. 27, 2014; dated Feb. 28, 2017.
Mackenzie, Kristian "Office Action", Canadian Application No. 2,705,670; dated Feb. 10, 2017.
Mackenzie, Kristian "Office Action", Canadian Application No. 2,705,647; dated Feb. 10, 2017.
Marcitech, Adam "NonFinal OA", U.S. Appl. No. 14/793,455, filed Jul. 7, 2015; dated May 3, 2017.
Pothier, Andrew "Office Action", Canadian Application No. 2,822,905; dated May 1, 2017.
"Third Office Action", Chinese Application No. 201280035240.4; dated Apr. 1, 2017.
*Medline Industries, Inc.* vs *C.R. Bard, Inc*; No. 14-cv-3618; Memorandum in Support of C.R. Bard's Motion for Leave to File Second Amended Answer to Add Counterclaim; Filed Sep. 25, 2015.
*Medline Industries, Inc.* vs *C.R. Bard, Inc*; No. 1:14-cv-03618; Defendant C.R. Bards, Inc's Second Amended Answer to Second Amended Complaint; Filed Sep. 25, 2015.
"DVD", Entitiled "*Preventing UTI: Care and Catheterization Techniques*"; Publication Date unknown but believed to be prior to 2007.
Cavanna, Mark "Final OA", U.S. Appl. No. 29/479,600, filed Jan. 17, 2014; dated Jun. 1, 2017.
Marcetich, Adam "Notice of Allowance", U.S. Appl. No. 14/793,455, filed Jul. 7, 2015; dated Jul. 20, 2017.
Poon, Robert, "Non-Final OA", U.S. Appl. No. 14/265,909, filed Apr. 30, 2014; dated Aug. 24, 2017.
Poon, Robert, "Notice of allowance", U.S. Appl. No. 15/067,903, filed Mar. 11, 2016; dated Aug. 24, 2017.

* cited by examiner

PATIENT EDUCATION: INFORMATION ABOUT CATHETERIZATION

1901

1. What is a urinary catheter?

A thin flexible tube that drains urine from the bladder into a collection bag.

The catheter helps:
   - When you can't urinate.
   - To measure how much urine you're producing.
   - During and after some surgeries or tests.

1902

2. What should you know about your catheter?

Only a trained provider inserts a catheter when necessary, and it is removed as soon as possible.
   - Caregivers must wash hands with soap or use alcohol-based rubs before and after touching your catheter.
   - If your caregivers don't clean their hands, it is o.k. to ask them to do so.
   - Do not disconnect the catheter yourself.
   - Ask every day whether you still need the catheter.

1903

3. Can you reduce your chances of getting an infection?

Absolutely!
   - Wash your hands before and after touching your catheter.
   - Make sure the tube is secured to your leg. Never twist, kink, or tug on it.
   - Always keep the collection bag below the level of your belly button.
   - Tell somebody whenever the bag is more than half full.

*FIG. 19*

PATIENT EDUCATION: INFORMATION ABOUT CATHETERIZATION

4. What is a 'catheter-associated' urinary tract infection (UTI)?

Some helpful germs live in our urinary tract. But if a catheter introduces 'outside' germs, they can cause an infection. That's why hands must be washed before handling your catheter. It's also why catheters must be removed as soon as possible.

— 2001

5. What are some symptoms if you have a urinary tract infection (UTI)?
- Sudden fever and/or bloody urine.
- Burning or painful urination, or pain below the stomach.
- Frequent, or more urgent, urinating after catheter is removed.

Tell your physician/provider right away, because an antibiotic may be needed.

— 2002

6. What about when you're going home?
- If you'll be using a catheter, make sure your health care provider fully explains how to care for it.
- Be sure to find out who to contact if you have questions after you get home.

— 2003

My physician's/provider's information: _____

Phone Number: _____

— 2004

Adapted from: Centers for Disease Control and Prevention. FAQs about "Catheter-Associated Urinary Tract Infection." Available at: http://www.cdc.gov/ncidod/dhqp/pdf/guidelines/CA-UTI_tagged.pdf. Accessed March 25, 2009.

©2009 Medline Industries, Inc., Silvertouch and Aloetouch are trademarks of Medline Industries, Inc. Assembled in USA by Medline Industries, Inc., Mundelein, IL. 60060-4486 USA. Distributed in Canada by Medline Canada Corp., Oakville, Ontario L2L6R2". www.medline.com 1-800-MEDLINE DYND160416 RG09/DYN 80759U

*FIG. 20*

FAMILY EDCATION

What you should know about your childs catheter.

1. What is a Urinary Catheter?

A thin flexible tube that drains urine from the bladder into a collection bag. The cathter helps:
   - When the child can't urinate an his or her own.
   - To closely measure how much urine the child is making.
   - During and after some surgeries and tests.

2. What to know about the child's catheter
   - Only a trained technician inserts a catheter when necessary, and it is removed as soon as possible.
   - Caregivers must wash hands with soap or use alchol-based sanitiser before and after touchng the catheter.
   - If caregivers don't clean their hands, polltely ask them to do so.
   - Do not remove or disconnect the catheter yourself and remaind the child not to touch the catheter.
   - Ask your caregiver after wheter the child still needs the cartheter.

3. What is a " cathter-associated urinary tract infection" (CAUTI)?

If a catheter introduces germs into the urinary tract, they can cause an infection. If a UTI develops, these symtams may appear:
   - Sudden fever.
   - Bloody urine.
   - Frequent or more urgent urinating after the catheter is removed.

4. Can you reduce changes of UTIs? yes!
   - Wash hands (yours, the caregiver's and the child's) before and after touching the cartheter.
   - Make sure the tube stays secured to the child's leg.
   - Make sure the collection bag stays below the level of the chld's belly button and off the floor.
   - Do not remove or disconnect the catheter yourself; only the trained caregiver, nurse or doctor should do this.
   - Ask daily whether the cartheter is still need.

MEDICAL KIT, PACKAGING SYSTEM, INSTRUCTION INSERT, AND ASSOCIATED METHODS

CROSS REFERENCE TO PRIOR APPLICATIONS

This application claims priority and benefit under 35 U.S.C. §119(e) from the following U.S. Provisional Applications: Ser. No. 61/352,140, filed Jun. 7, 2010; Ser. No. 61/352,155, filed Jun. 7, 2010; Ser. No. 61/428,944, filed Dec. 25, 2010; and Ser. No. 61/437,796, filed Jan. 31, 2011, each of which is incorporated herein by reference.

This application is a continuation in part of, and therefore claims priority to, U.S. patent application Ser. No. 12/495,148, filed Jun. 30, 2009, which is incorporated herein by reference. This application is a continuation in part of, and therefore claims priority to, U.S. patent application Ser. No. 12/647,515, filed Dec. 27, 2009, which is incorporated herein by reference.

This application is related to commonly assigned U.S. Pat. No. 7,624,869 to Primer, which is incorporated herein by reference. This application is related to commonly assigned U.S. patent application Ser. No. 12/004,796, filed Dec. 21, 2007, which is incorporated herein by reference.

BACKGROUND

Technical Field

Embodiments of the invention relate generally to a patient aid for ensuring proper dissemination of information relating to medical procedures, and in one or more embodiments, to a patient aid suitable for inclusion in a medical kit used for medical procedures that ensures the information is delivered to the patient undergoing the procedure.

Background Art

In a healthcare setting, patients need education regarding their ailment, treatment, or steps the patient needs to take after they have left the healthcare services. The healthcare provider does not always give the patient the proper information, or in some cases does not give any information at all. People undergoing medical procedures are thus frequently left without information regarding their condition, the treatment that has been administered, or how to care for themselves post-treatment. Without the proper post-treatment information, patients are at risk for infection, developing secondary medical issues, or compromising the procedure's effectiveness.

In some cases, the person is discharged from care while either still receiving treatment. For example, the person may require the use of home care devices to continue the treatment steps after discharge. Alternatively, the person may be discharged with a medical device when the treatment is not completed while under the immediate supervision of the caregiver. While educational materials may be available, it is frequently the case that the material fails to reach the intended target, i.e., the patient. When the necessary educational material does not reach the patient, they are left without critical information allowing the appropriate care to be administered either by themselves or others, which may lead to further illnesses or complications of a present condition.

There is a need for an improved information dissemination system and method.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and to explain various principles and advantages all in accordance with the present invention.

FIGS. 19-21 illustrate examples of patient information suitable for inclusion with a patient aid configured in accordance with one or more embodiments of the invention.

Figure 1:
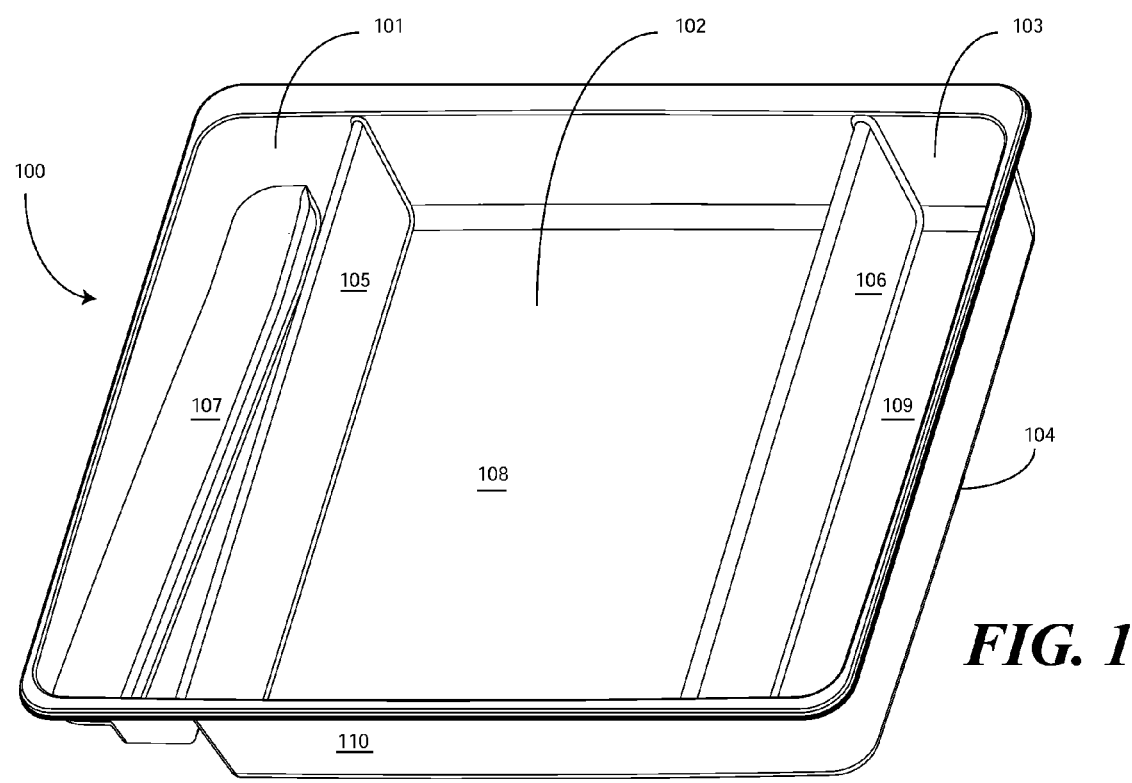
FIG. 1 one embodiment of a tray for use in a medical procedure kit in accordance with one or more embodiments of the invention.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION OF THE INVENTION

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, and the like may be used solely to distinguish one entity or action from another entity or action without necessarily requiring or implying any actual such relationship or order between such entities or actions. Also, reference designators shown herein in parenthesis indicate components shown in a figure other than the one in discussion. For example, talking about a device (10) while discussing figure A would refer to an element, 10, shown in figure other than figure A.

Embodiments of the invention provide a patient aid that is suitable for inclusion with medical device kits. The patient aid provides necessary patient information corresponding to a particular medical procedure. It is highly important that patients undergoing medical treatment or procedures be given the proper information relating to the procedure, post-procedure care, and follow-up actions. However, even when medical device manufacturers provide the necessary information, it can sometimes be difficult for a health care services provider to differentiate between that which is to be retained by the health care services provider and that which is to be delivered to the patient. Said differently, it is frequently difficult to visually discern whether a particular leaflet, printed material, or handout is to be given to the patient. In other cases the health care provider is simply unaware of the availability of the information.

Embodiments of the present invention provide a solution to the problems cited in the preceding paragraph by providing a patient aid, suitable for inclusion within a medical kit, that includes patient education information relating to a particular medical procedure. While health care services provider information is also included, in one embodiment the information for the health care services provider is physically separate from the patient aid. Additionally, to make recognition easier, the patient aid is configured with a greeting card appearance, activity sheet appearance, or other graphical indicia that indicates that the patient aid is intended for the patient. The appearance of the patient aid also serves to indicate that the patient aid should be delivered to the patient.

In one embodiment, the patient aid is configured with pediatric patient education material so as to be aesthetically pleasing and entertaining to children. In another embodiment, the patient aid comprises a greeting card appearance on an outward facing portion, with patient information being disposed inside, so as to be aesthetically pleasing and comforting to adults. The pediatric patient education material and greeting card are but two illustrative examples patient aids suitable for inclusion with medical procedure kits as described herein. It will be clear to those of ordinary skill in the art having the benefit of this disclosure that other aesthetically pleasing, entertaining, and/or comforting disguises for patient education information may be created without departing from the spirit and scope of the disclosure.

Where the patient aid is included with a medical procedure kit, in one embodiment a label, intended for the health care services provider, is configured with indicia indicating that a patient aid is enclosed. The label, which can be configured as a first portion of the health care services provider information or as a booklet, can be applied to the surrounding packaging material. For example, in a pediatric medical procedure kit, a printed label can be adhesively affixed to a layer of packaging material, with the printed label having disposed thereon a caricature indicating that the medical procedure kit is intended for pediatric use and includes pediatric material. The caricature reminds the health care services provider that not only is patient education information included, but also that the patient education information should be delivered to the user. Other reminders and mnemonic devices can be included as well. For example, in one embodiment the printed label is configured as a booklet having pressure sensitive adhesive disposed between the pages. When the pages are opened, a "CSHH-HHHKKKK" sound emanates. In one embodiment, providers of the medical procedure kit instruct health care services providers to "remember, whenever you hear that sound, there is patient education material that needs to be given to the patient." Accordingly, the audible sound serves as a mnemonic indicating that the patient aid should be given to the patient.

In one embodiment, the patient aid comprises a first portion and a second portion, both of which are either carried on, disposed on, or coupled to a carrier. The first portion is an outwardly visible portion and the second portion is an education portion. The education portion is configured with an informational set related to medically educating the intended recipient, i.e., the patient. The first portion can be configured to be aesthetically pleasing, entertaining, and/or comforting. Accordingly, the first portion forms somewhat of a disguise for the information set, in that it softens and eases the delivery of medical information. As noted, in one embodiment the first portion is configured as having a greeting card appearance. In another embodiment, the first portion can be configured as an activity card. The patient aid can then be folded such that the first portion faces outward and the second portion faces inward. The patient education aid provides the patient, or those associated with assisting the patient, with education on the procedure performed on the patient as wells as care instructions for the patient or relative to administer subsequent to leaving professional care.

The embodiments described herein work to facilitate delivery of this information to the patient, thereby reducing hospital readmissions, improving patient satisfaction, promoting self care and preventative healthcare, and improving patient compliance with medical instructions. Additionally, the labels, configurations, and mnemonic devices described herein work to prevent the patient education information from being thrown away inadvertently. In short, embodiments described herein get health care services providers to simply notice that patient education information is included to be given to the patient. The aesthetically pleasing, entertaining, and/or comforting appearance not only gets the health care provider to notice the patient education material, but also facilitates making them actually desire to provide the information to the patient.

In one or more embodiments, the patient aid, be it pediatric or adult, is included with a medical procedure kit that includes medical products, devices, and assemblies for performing a medical procedure. For illustration only, and for simplicity of description, a catheterization medical procedure kit will be used as an example to describe features and benefits of embodiments of the invention. However, it will be clear to those of ordinary skill in the art having the benefit of this disclosure that embodiments of the invention are not so limited. Other medical procedure kits for performing other procedures could be substituted for the illustrative catheterization tray disclosed herein by substituting other medical implements for the catheterization implements.

In the illustrative embodiment, the medical procedure kit comprises a tray with one or more medical devices or assemblies disposed therein. It will be understood that the tray can be substituted with other containment devices. Further, it will be understood that the tray can be configured to be generically shaped or procedure-specifically shaped. For example, when the medical procedure kit is configured for a catheterization procedure, the tray can be configured as a single container configured to accommodate not only the catheter assembly and fluid bag, but also syringes containing sterile water or lubricants. Further, the tray can accommodate a sterile specimen jar for capturing samples taken from the patient via the catheter. In addition to simply accommodating these corresponding medical devices, in one embodiment the tray is configured to provide the medical services provider with instructions and with mnemonic devices indicating in which order to use each device. For example, a compartment containing syringes, in one embodiment, includes an inclined, stair-stepped bottom member to present the plungers of each syringe at an easy to reach angle and at different heights based upon order of use.

Another advantage of using a tray in the medical procedure kit in various embodiments of the present invention is that compartments can be configured with multi-purpose functionality. For example, in one catheterization embodiment, a container configured to accommodate a syringe having lubricating jelly can also be configured for use as a lubricating jelly applicator. Illustrating by example, a medical or health care services provider first dispenses the lubricating jelly into the syringe compartment. The medical services provider then passes the catheter from another compartment through an opening in a barrier separating the compartments into the lubricating jelly. As such, the tray not only serves as a shipping and storage container for an assembly of devices, including the patient aid, that are used with a catheterization procedure, but also as an application device to assist a medical services provider in using those products together.

Figure 22:
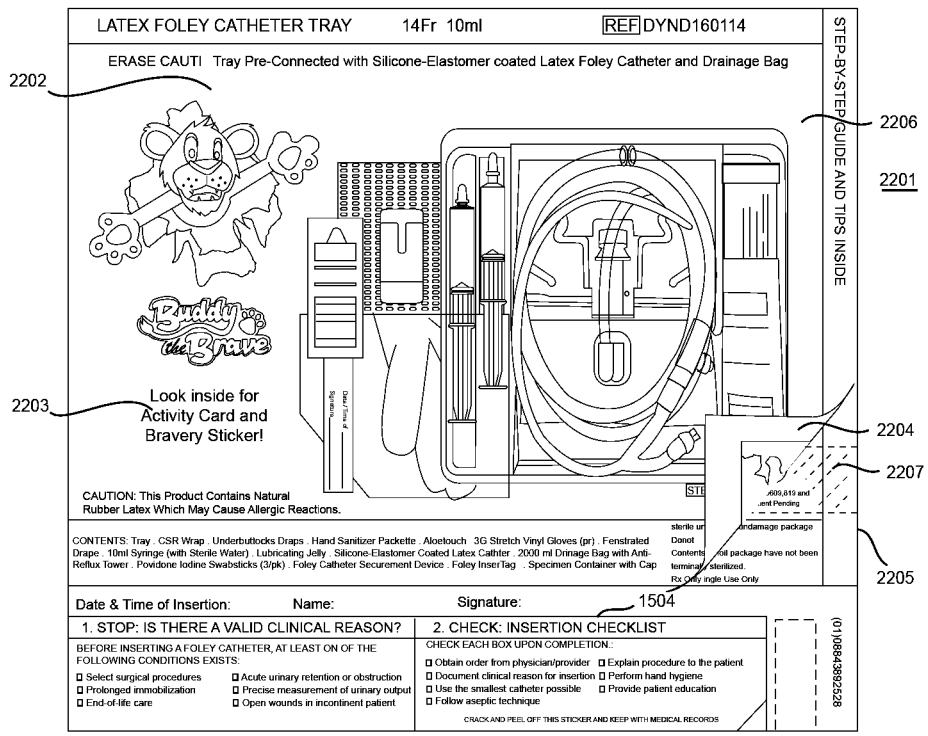
FIGS. 22-23 illustrate examples labeling that can be included with medical procedure kits configured in accordance with one or more embodiments of the invention.
Figure 23:
Figure 24:
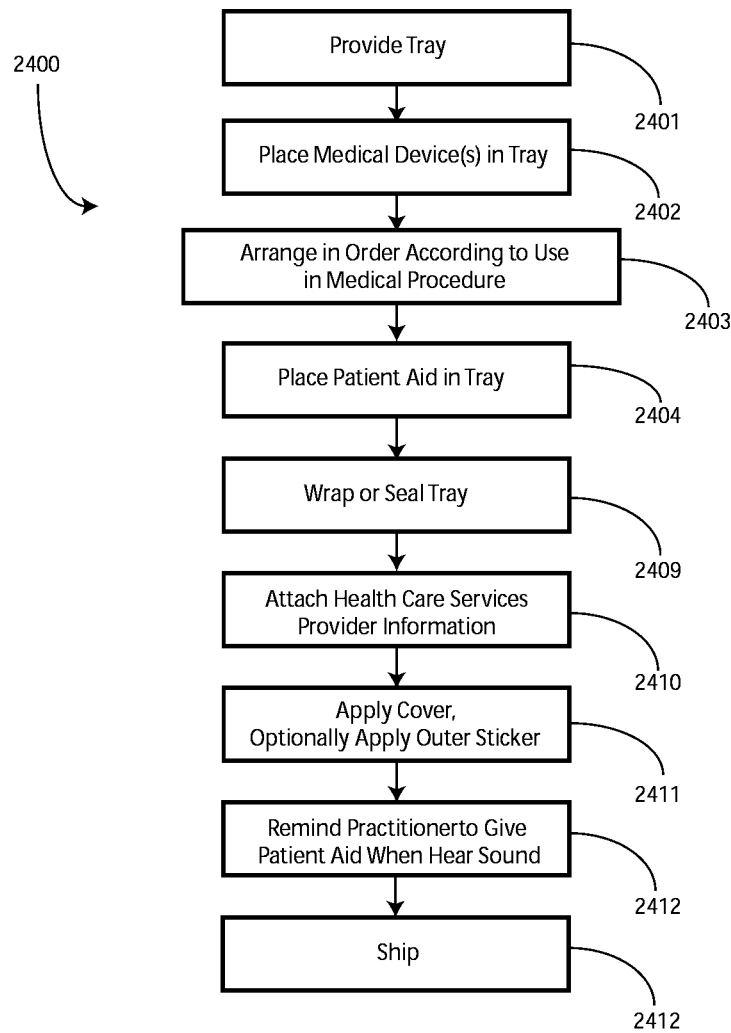
FIGS. 24-25 illustrate methods for making and using, respectively, medical procedure kits in accordance with one or more embodiments of the invention.
Figure 25:
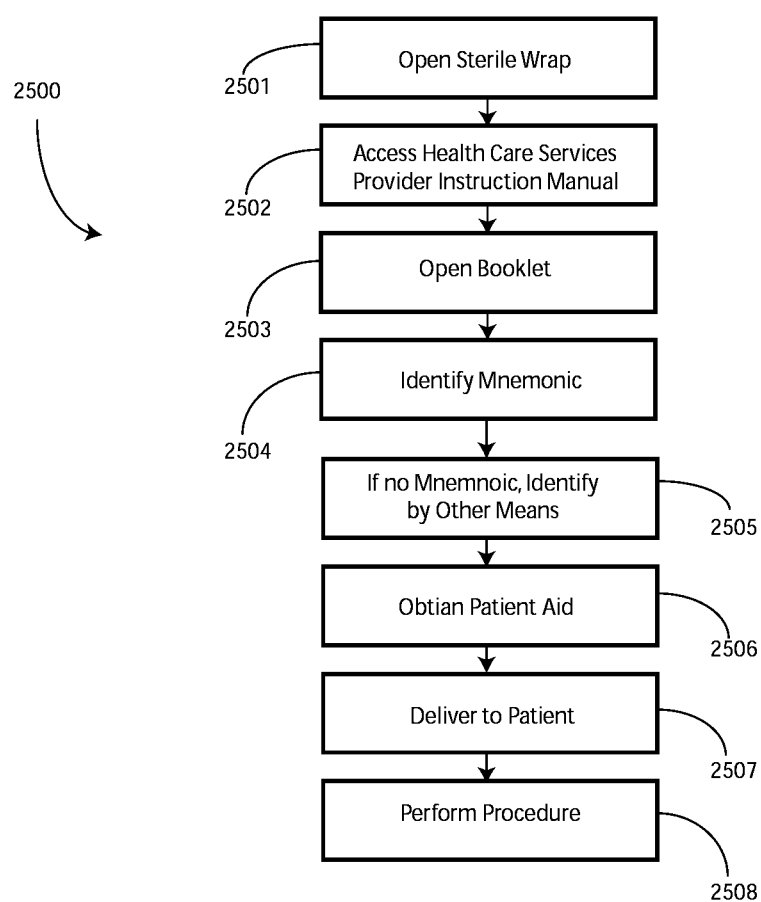

In the figures below, FIGS. 1-2 will describe examples of containers used in medical procedure kits, while FIGS. 3 and 4 will describe illustrative medical procedure kits suitable for use with patient aids and health care services provider information configured in accordance with embodiments of the invention. FIG. 5 will illustrate a generic patient aid, while FIGS. 6-9 will describe illustrative embodiments. FIGS. 10-14 will describe illustrative methods for packaging medical procedure kits. FIGS. 15-18 will describe illustrative health care services provider information, while FIGS. 19-21 will describe information suitable for inclusion with a patient aid. FIGS. 22-23 will then describe examples of labeling that can be included with medical procedure kits when patient aids are included therewith. FIGS. 24-25 will describe methods for making and using, respectively, medical procedure kits in accordance with one or more embodiments of the invention.

Turning first to FIG. 1, illustrated therein is a container suitable for carrying medical devices in a medical procedure kit. The illustrative container of FIG. 1 is configured as a tray 100, although, as noted above, other containers may be substituted without departing from the spirit or scope of the invention.

FIG. 1 illustrates a top, front right perspective view of the tray 100. The tray 100, in one embodiment, is formed by a contoured surface 104 that defines the various features and compartments of the tray 100. The features and compartments will vary based upon the particular medical procedure for which the tray 100 is designed. For instance, a tray for a catheterization procedure may be different from a tray configured for use in a blood-sampling procedure.

The contoured surface 104 of the tray 100 can be manufactured in various ways. For example, in one embodiment, the tray 100 can be thermally formed on a mold from a soft thermoplastic, such as styrene or polystyrene. In another embodiment, the tray 100 can be injection molded. In another embodiment, the tray can be poured on a mold using a quick setting plastic, epoxy, or resin. Other methods of manufacture will be obvious to those of ordinary skill in the art having the benefit of this disclosure.

In this generic embodiment, the illustrative tray 100 includes three main compartments: a first compartment 101, a second compartment 102, and a third compartment 103. The first compartment 101 is separated from the second compartment 102 by a first barrier 105. The second compartment 102 is separated from the third compartment 103 by a second barrier 106.

In one embodiment, the compartments 101,102,103 are open from the top of the tray 100 and are bounded on the bottom by a first base member 107, a second base member 108, and a third base member 109. The compartments are bounded on the sides by a perimeter wall 110. In the illustrative "open top" embodiment of FIG. 1, the perimeter wall 110 ends in a horizontal flange 111 extending substantially orthogonally from the perimeter wall 110. It will be clear to those of ordinary skill in the art having the benefit of this disclosure that embodiments other than that shown in FIG. 1 are possible without departing from the spirit and scope of the invention. For instance, the top of the tray 100 could have a hinged or snap-coupled lid that is opened or removed to reveal the compartments there beneath.

In one illustrative embodiment, the tray 100 is configured to hold or otherwise accommodate all of the necessary devices and materials to perform a medical procedure. Further, as will be shown below, the tray 100 can be configured to hold the patient aid in different places as well. For example, in one embodiment, the patient aid will be disposed atop the medical devices. In another embodiment, the patient aid can be tucked within cover material. Other locations will be obvious to those of ordinary skill in the art having the benefit of this disclosure.

Some prior art medical procedure kits ship products in multiple containers. These prior art systems may contribute to substandard techniques in that sterile fields can be contaminated when moving devices from shipping container to procedure site. Consequently, the patient can be at an elevated risk of infection. However, when the compartments 101,102,103 are included, all devices can be included in a single level tray 100. This helps to minimize the risk of contaminating the patient or the sterile field during the procedure. The compartmentalized configuration, which includes all the necessary medical devices for a procedure in one embodiment, helps to reduce the risk of contaminating a patient or compromising the sterile nature of the components stored in the tray 100. Further, the risk of cross-contamination between sterile work areas and non-sterile spaces is minimized.

In one embodiment, instructions or other graphical indicia can be printed, placed upon, or molded into the horizontal flange 111. For example, compartment designations can be placed above each compartment 101,102,103 to ensure the medical services provider uses the correct device or material at the correct time. In another embodiment, expiratory dates for materials or devices disposed within the tray 100 may be placed on the horizontal flange 111. It will be obvious to those of ordinary skill in the art having the benefit of this disclosure that the invention is not so limited. Any number of various text or picture combinations can be printed on, placed upon, or molded into various parts of the tray. For instance, graphical indicia can be applied to the compartment base members in addition to the horizontal flange 111. Note that the horizontal flanges, in one embodiment, can terminate in downwardly protruding vertical flanges for increased stability during the printing process.

Figure 2:
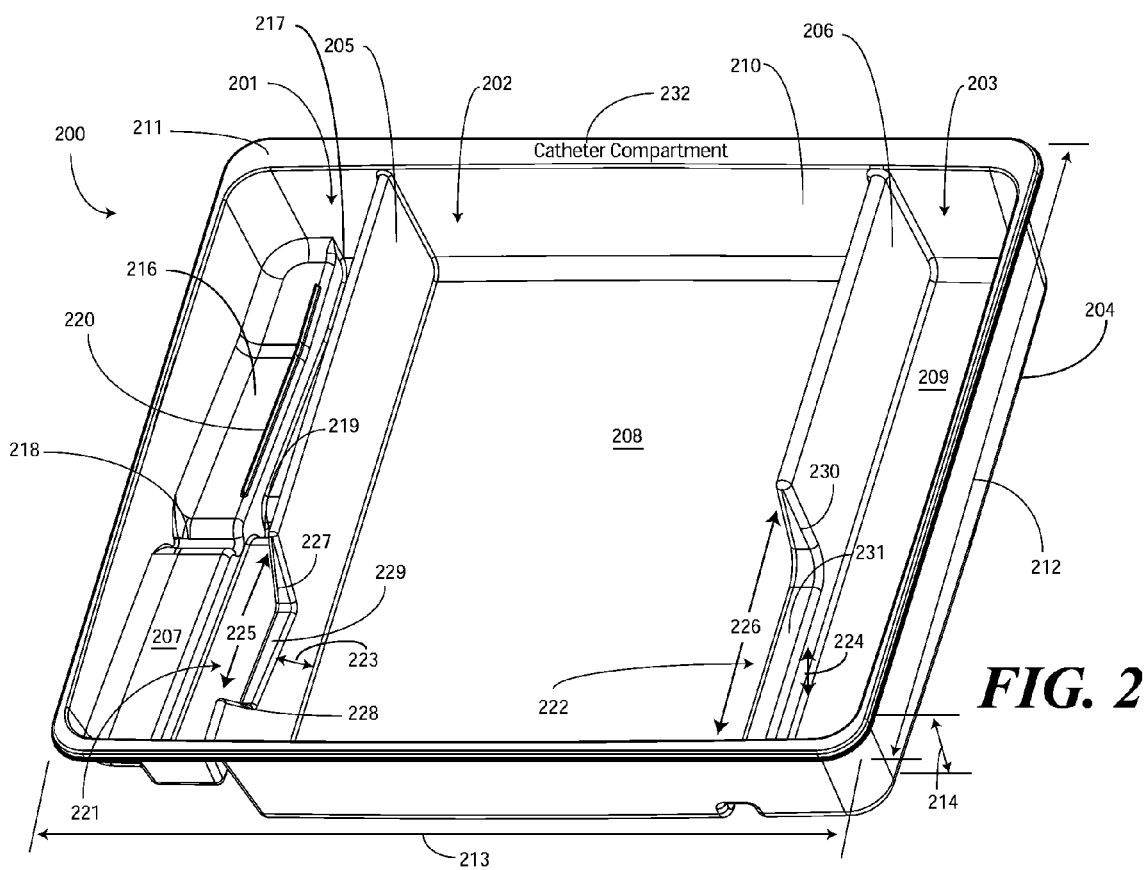
FIG. 2 illustrates one embodiment of a tray for use in a catheter procedure kit, or similar kit, configured in accordance with one or more embodiments of the invention.

Turning now to FIG. 2, illustrated therein is another tray 200 that is configured specifically for one illustrative type of predetermined medical procedure. As noted above, for illustration purposes, the procedure described will be that of catheterization.

The tray 200, in one embodiment, is formed by a contoured surface 204 that defines the various features and compartments of the tray 200. Exemplary dimensions for one embodiment of the tray 200 are as follows: The length 212 can be between nine and twelve inches, such as ten inches. One illustrative length 212 may be 10.380 inches. Similarly, the width 213 can be between eight and eleven inches, such as nine inches. One illustrative width 213 is 9.250 inches. The height 214 can be between one and three inches. One illustrative height 214 is 1.750 inches.

In the illustrative embodiment of FIG. 2, the tray 200 includes three main compartments: a first compartment 201, a second compartment 202, and a third compartment 203. The first compartment 201 is separated from the second compartment 102 by a first barrier 205. The second compartment 202 is separated from the third compartment 203 by a second barrier 206.

In one embodiment, the compartments are open from the top of the tray 200—the top being opposite the base members of the tray 200—and are bounded on the bottom by a first base member 207, a second base member 208, and a third base member 209. The compartments are bounded on the sides by a perimeter wall 210. In the illustrative "open top" embodiment of FIG. 2, the perimeter wall 210 ends in a horizontal flange 211 extending substantially orthogonally from the perimeter wall 210. It will be clear to those of ordinary skill in the art having the benefit of this disclosure that embodiments other than that shown in FIG. 2 are possible without departing from the spirit and scope of the invention. For instance, the top of the tray 200 could have a hinged or snap-coupled lid that is opened or removed to reveal the compartments there beneath.

In one illustrative embodiment, the tray 200 is configured to hold or otherwise accommodate all of the necessary devices and materials to perform a catheter-based procedure on a patient. Said differently, the tray 200 is configured to hold not only the catheter assembly, but the medical devices corresponding to catheter use as well. Using one illustrative procedure as an example, the following devices will be used: a syringe holding sterile water, a syringe holding lubricating jelly or another equivalent lubricant, a catheter assembly, skin cleansing or preparation materials, and a specimen jar. The various compartments and features of the tray 200 shown in FIG. 2 will be described for use with these devices. As will be described in more detail below, additional objects can be included with the tray, such as one or more towels, a drape to cover the patient, rubber gloves, hand sanitizing materials, swab sticks, a securement device, a Foley insert tag, a printed instruction pamphlet, and so forth. The syringe holding sterile water, syringe holding lubricating jelly, catheter assembly, and specimen jar are used for illustration purposes only, as it will be clear that other objects may be added to or substituted for these objects. Further, subsets of these objects may be used.

In one embodiment suitable for procedures using the syringe holding sterile water, syringe holding lubricating jelly, catheter assembly, and specimen jar, in one embodiment, the tray 200 is configured such that these objects are ordered in accordance with their use during the procedure. For example, in one embodiment the tray 200 includes a first compartment 201 for accommodating one or more syringes, a second compartment 202 for accommodating the catheter assembly, and a third compartment 203 for accommodating the specimen jar. These devices stowed in the various compartments will be illustrated and described with respect to FIG. 4 below.

For example, in one embodiment the first compartment base member 207 includes a stair-stepped contour 215 suitable for accommodating a plurality of syringes at different heights. For example, a first step portion 216 of the stair-stepped contour 215 may be at a different height within the tray 200 than a second step portion 217 of the stair-stepped contour. In the illustrative embodiment of FIG. 2, the first step portion 216—which is disposed farther from the first barrier 205 than the second step portion 217—is shallower than the second step portion 217. Said differently, the second step portion 217 is disposed at a greater depth within the tray 200 than the first step portion 216.

The stair-stepped contour 215 can be used as mnemonic device when multiple syringes are stored within the first compartment 201. For example, it may be intuitive that a syringe placed on a higher step portion may need to be used first. This intuition is further enforced when the higher step portion is disposed farther to the left in a left-to-right usage configuration. Thus, a user receives a mnemonic reminder to use a syringe disposed on the first step portion 216 prior to a syringe disposed on the second step portion 217, as it is both higher and farther to the left.

Where syringes are stowed in the first compartment 201, the first compartment base member 207 can further be configured for syringe ease of use. For example, in one embodiment the first compartment base member 207 is inclined relative to other compartment base members. In the illustrative embodiment of FIG. 2, the second compartment base member 208 and third compartment base member 209 are substantially coplanar with each other. Further, the second compartment base member 208 and third compartment base member 209 are generally flat, although it will be clear to those of ordinary skill in the art having the benefit of this disclosure that contours could be incorporated into one or both of these base members.

In this illustrative embodiment, however, the first compartment base member 207 is configured to be inclined relative to one or both of the second compartment base member 208 and third compartment base member 209. As such, the stair-stepped contour 215 forms a ramp upon which syringes may be placed so that the plunger of each syringe is predisposed to project upward and out of the tray 200. Said differently, the stair-stepped contour 215 is configured such that the first step portion 216 and the second step portion 217 are disposed in a non-parallel orientation relative to the second compartment base member 208. This configuration makes it easier for a medical services provider to grasp the syringes and remove them from the tray 200.

The first compartment base member 207 may include other features suitable for accommodating one or more syringes as well. In one embodiment, one or both of the first step portion 216 and second step portion 217 include recesses 218,219 for accommodating a syringe flange. These recesses 218,219 generally function to prevent the syringes from sliding lengthwise within the first compartment 201. Similarly, in one embodiment one or both of the first step portion 216 and the second step portion 217 include protrusions 220 that help to prevent the syringes from sliding laterally within the first compartment 201.

In one embodiment, one or both of the first barrier 205 and the second barrier 206 include openings disposed therein. In the illustrative embodiment shown in FIG. 2, the first barrier 205 includes a first opening 221 between the first compartment 201 and the second compartment 202. Similarly, the second barrier 206 includes a second opening 222 between the second compartment 202 and the third compartment 203. Each of these openings has an opening depth associated therewith. Similarly, each opening has an opening width associated therewith. In the illustrative embodiment of FIG. 2, the first opening 221 is bounded by a first opening base member 229 and two inclined first opening side members 227,228, while the second opening 222 is bounded by a second opening base member 231, an inclined second opening side member 230, and the perimeter wall 210.

While the opening depths can be the same, in one embodiment the opening depths are different. For example, in the illustrative embodiments of FIG. 2, the first opening 221 has a first opening depth 223 that is less than the second opening depth 224 of the second opening 222. Similarly, in one embodiment the opening widths are different. For example, in the illustrative embodiments of FIG. 2, the first opening 221 has a first opening width 225 that is less than the second opening width 226 of the second opening 222. Such a disparity in opening depths and widths, as well as the inclusion of inclined opening side members, provides an advantage in some applications.

For instance, in many catheter procedures a pair of syringes—such as syringes having a one-half inch diameter—fits easily into the first compartment 201 when the tray 200 is made with the illustrative dimensions set forth above. However, some procedures require one or more of the syringes to be larger. For example, some syringes are larger in diameter. These larger syringes are capable of nesting within the first opening 221 and second opening 222. The inclined opening side members prevent the syringe from moving lengthwise, while the disparate opening heights present the plunger of the syringe to the medical services provider for easy removal from the tray 200.

The stair-stepped contour 215, working in tandem with the first opening 221, gives the tray additional advantages over prior art catheter containers. For instance, when the first compartment 201 has a first compartment base member 207 configured with a stair-stepped contour 215, the first compartment 201 can be used as a lubricant applicator for the catheter.

Specifically, the medical services provider may dispense the lubricating jelly along the second step portion 217. As the second step portion 217 is lower in the tray 200 than the first step portion 216, the second step portion 217 serves as a channel in which the lubricating jelly may spread. A health care services provider may then pass the catheter through the first opening 221, through the channel formed by the second step portion 217, i.e., along the second step portion 217 through the dispensed lubricating jelly, and out the top of the tray 200 to the patient. This feature of the tray 200 greatly eases the application of lubricating jelly to the catheter when compared to prior art solutions. In one embodiment, the tray 200 is packaged with printed instructions showing the medical services provider how to apply lubricating jelly in this manner. The printed instructions will be described in more detail below.

It will be clear to those of ordinary skill in the art having the benefit of this disclosure that alternative methods may be used to apply the lubricating jelly as well. For example, in another embodiment, the lubricating jelly is dispensed directly onto the catheter tubing while the tubing is in or above the first compartment 201. Excess lubricant falling from the catheter tubing can then collect, and be retained, in the second step portion 217.

This particular feature highlights another advantage of the "compartmentalized" structure of various embodiments of the invention. As the tray 200 includes multiple compartments, various tasks associated with a catheterization procedure can be completed while keeping the catheter within the tray 200. The ability to keep the catheter in the tray 200 reduces the risk that the catheter or corresponding devices will be contaminated with bacteria or microbes on other objects within the procedure room. For example, when the first compartment 201 is used to apply lubricating jelly to the catheter, the lubricating jelly can be applied while the catheter is contained within the tray 200, thereby reducing the risk that the catheter will become contaminated. This correspondingly reduces the risk of infection for the patient receiving the catheter.

Prior art systems, for example such as those in which the catheterization procedure components are shipped in separate containers, may contribute to substandard techniques in that the catheter can become contaminated when moving it from its shipping container. Consequently, the patient can be at an elevated risk of infection as the catheter is moved from one tray to another. Embodiments of the present invention solve this problem by providing a single level tray 200 with compartments. Further, in one embodiment the first compartment 201 includes the first opening 221 so the catheter can stay in place during and after lubrication. By having easy access to the components disposed in the single level tray 200, the medical services provider can more easily prepare and use the components within the tray 200. This helps to minimize the risk of contaminating the patient or the sterile field during the procedure.

In one embodiment, the second step portion 217 is configured to be inclined at a shallower angle than the first step portion 216 in at least a portion opposite the recess 219 from the first opening 221. When configured in such a fashion, the second step portion 217 includes a "cutdown" so that the catheter can stay within the channel both during and after lubrication.

Additionally, the catheter can be placed in both the first opening 221 and second opening 222 during lubrication. When positioned in this configuration, the second opening 222 helps to align the catheter with the first opening for easy passage through the lubrication channel formed by the second step portion 217.

The tray 200 of FIG. 2 includes additional advantages over prior art catheter packaging as well. For example, in one embodiment, instructions 232 or other graphical indicia can be printed, placed upon, or molded into the horizontal flange 211. In one embodiment, compartment designations can be placed above each compartment to ensure the medical services provider uses the correct device or material at the correct time. In another embodiment, expiratory dates for materials or devices disposed within the tray 200 may be placed on the horizontal flange 211. It will be obvious to those of ordinary skill in the art having the benefit of this disclosure that the invention is not so limited. Any number of various text or picture combinations can be printed on, placed upon, or molded into various parts of the tray. For instance, graphical indicia can be applied to the compartment base members in addition to the horizontal flange 211. Note that the horizontal flanges, in one embodiment, can terminate in downwardly protruding vertical flanges for increased stability during the printing process.

Another advantage of the tray 200 is that its compartmentalized configuration helps to reduce the risk of contaminating a patient or compromising the sterile nature of the components stored in the tray 200. Since both the catheter assembly and medical devices corresponding to catheter use are stored within the same tray 200, the risk of cross-contamination between sterile work areas and non-sterile spaces is minimized. Further, by having the catheter assembly and the devices corresponding to catheter use stowed in a one-level tray rather than a multi-level, stacked configuration, the medical services provider can more easily prepare and use the catheter and corresponding devices disposed within the tray 200.

Figure 3:
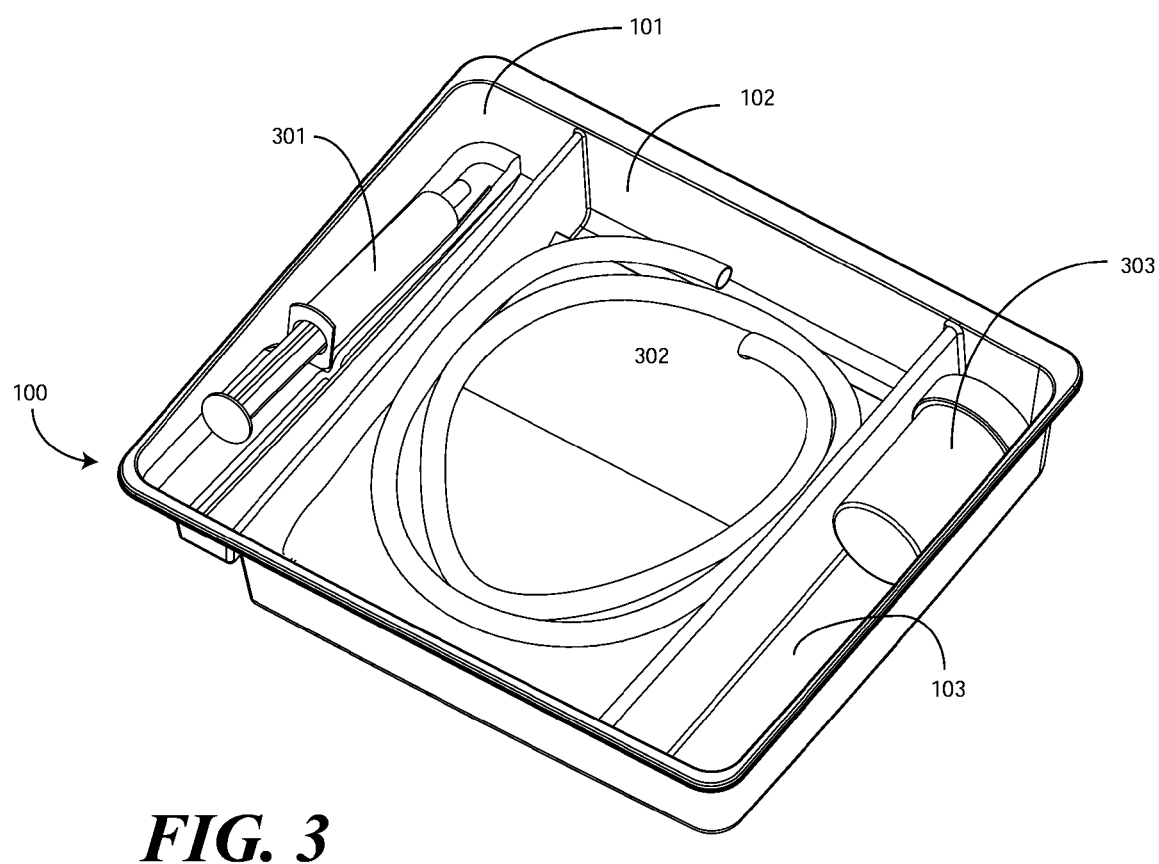
FIG. 3 illustrates a generic medical procedure kit configured in accordance with embodiments of the invention.

Turning now to FIG. 3, illustrated therein is the generic tray 100 of FIG. 1 having one or more medical assemblies or devices needed for use in a medical procedure disposed therein. Different devices can be disposed in different compartments, as will be readily understood by those of ordinary skill in the art having the benefit of this disclosure. The illustrative devices shown in FIG. 3 are for a fluid sampling procedure, and include a syringe 301, a tourniquet 302, and a specimen jar 303. The devices are disposed in various compartments of the tray. In this illustration, the syringe 301 is disposed in the first compartment 101, while the tourniquet 302 is disposed in the second compartment 102. The specimen jar 303 is disposed in the third compartment 103.

Figure 4:
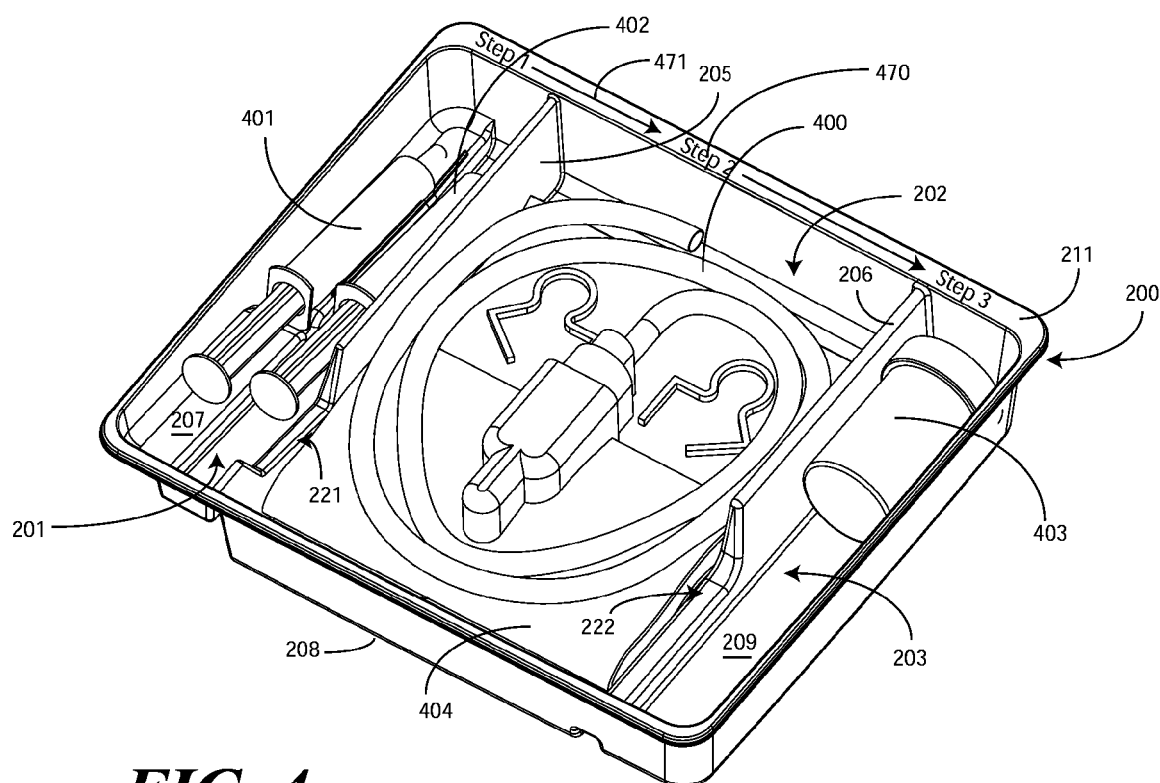
FIG. 4 illustrates a medical procedure kit configured for a catheterization procedure in accordance with one or more illustrative embodiments of the invention.
Figure 5:
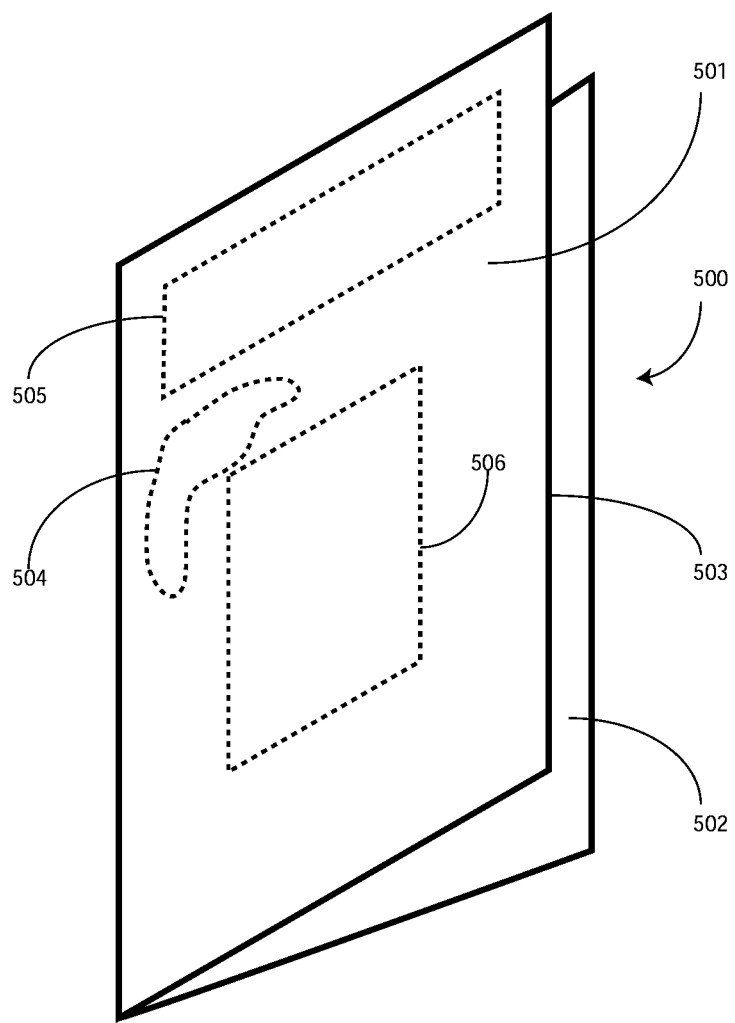
FIG. 5 illustrates a generic patient aid configured in accordance with one or more embodiments of the invention.

Turning now to FIG. 4, illustrated therein is the tray 200 of FIG. 2, having medical devices used in a catheterization procedure. In this illustrative embodiment, the tray 200 has disposed therein a catheter assembly 400, syringes 401,402, and a specimen container 403. In this illustrative embodiment, the first compartment 201 is configured to accommodate syringes 401,402. The second compartment 202 is configured to accommodate a coiled medical device, such as catheter assembly 400. The third compartment 203 is configured to accommodate the specimen container 403. The third compartment 203 can accommodate other materials as well, including skin sanitizers and cleansing liquids, solutions, or gels. As mentioned above, additional devices corresponding to catheter use, including towels, drapes, rubber gloves, and so forth, can be disposed in the tray 200 as well. As an illustration of this flexibility, a towel 404 is disposed beneath the catheter assembly 400.

As noted above, in one embodiment the flange 211 can include instructions 470 or other graphical indicia. As also noted above, the implements disposed in the various compartments 201,202,203 can have implements therein arranged in accordance with use. In one embodiment, shown illustratively in FIG. 4, the instructions 470 can be coordinated with this arrangement, indicating that components disposed in the first compartment 201 should be used first, components disposed in the second compartment 202 should be used next, and so forth. To assist the user in understanding workflow, arrows 471 or other directional elements can be included on the flange 211 as well.

Syringes 401,402 are disposed in the first compartment, with one syringe 401 being supported at a different elevation within the tray than the other syringe 402. The different elevations can be relative to each syringe 401,402, or to other components of the tray 200, such as the second compartment base member 208. Said differently, one syringe 401 is supported by the first compartment base member 207 at a shallower depth within the tray 200 than the depth of the second compartment base member 208. Further, where the first compartment base member 207 is inclined relative to other base members, one or both syringes 401,402 will be supported in a non-parallel configuration relative to the second compartment base member 208. A large syringe (not shown) can be supported laterally within the tray 200 when it is placed across the tray 200 such that it lies within both the first opening 221 of the first barrier 205 and the second opening 222 of the second barrier 206. Such a syringe will pass across the top of the catheter assembly 400, but will be held in place by the side members of each opening.

Turning now to FIG. 5, illustrated therein is one embodiment of a patient aid 500 configured in accordance with one or more embodiments of the invention. In one embodiment, the patient aid 500 is configured as a standalone device suitable for delivery to patients. In such an embodiment, the patient aid 500 is physically separate from health care provider information, which is included in or at other locations in a medical procedure kit. In one embodiment, the patient aid 500 is designed for inclusion with a medical procedure kit, such as those shown in FIGS. 3 and 4 above.

In one embodiment, the patient aid 500 is configured as an educational card or pamphlet comprising a first portion 501 and a second portion 502, both of which are either carried on, disposed, on or coupled to a carrier 503. The first portion 501 is an outwardly visible portion, while the second portion 502 faces inwardly. In one embodiment, the first portion 501 is configured with a disguise so as to be any of aesthetically pleasing, entertaining, and/or comforting in appearance. In one embodiment, the second portion 502 is configured as an education portion.

In one embodiment, the patient aid 500 is associated with medical procedures and/or medical devices. Accordingly, the second portion 502 can be configured to have an informational set disposed thereon related to educating the intended recipient. The informational set can comprise any of the following: educational information corresponding to a medical procedure, patient care information corresponding to a medical procedure, information relating to a medical device, such as a urinary catheter, peripherally inserted central catheter, or wound dressing, that is applied to the patient, an illustrated guide depicting patient care for medical devices, or combinations thereof.

In the illustrative embodiment of FIG. 5, the patient aid is configured as a folded card that has the first portion 501 facing outwardly and the second portion 502 facing inwardly. It will be clear to those of ordinary skill in the art having the benefit of this disclosure that other folding configurations could also be used, including tri-folds, quad-folds, and so forth. In one embodiment, the first portion 501 and the second portion 502 are detachable from each other. In another embodiment, they are integrated with the carrier 503 so as to not be readily detachable.

To provide an aesthetically pleasing, entertaining, and/or comforting appearance, in one embodiment the outward facing portion is configured with a greeting card appearance, while the inward facing portion comprises patient information relating to a medical procedure, medical device, post-procedure medical care, or post-procedure medical device care. In another embodiment, configured primarily for children, the outward facing portion is configured as an activity card, with the inward facing portion being configured with the patient information, which includes educational information corresponding to a medical procedure. The patient aid 500 provides the patient, or those associated with assisting the patient, with education on the procedure performed on the patient as wells as care instructions for the patient or relative to administer subsequent to leaving professional care.

To further provide an aesthetically pleasing, entertaining, and/or comforting appearance, the first portion 501 can be configured in a variety of ways. For example, in one embodiment, the first portion 501 includes one or more healing colors 504 disposed thereon or integrated therein. In another embodiment, the first portion 501 has a greeting 505 disposed thereon. In one embodiment, the greeting 505 is configured in large-font type, i.e., fonts in excess of 14-point fonts, so as to be readily readable by a person with less than perfect eyesight.

In one embodiment, the first portion 501 comprises a picture 506, which can be a serene landscape, flowers, candy, animals, and so forth. These features work to make the patient aid 500 different in appearance so that it stands out to health care services providers. The features also work to create an emotional connection with the health care services provider, as well as appositive reaction from the patient. Additionally, even if a patient or health care services provider places the patient aid 500 on a bedside table, the outward appearance increases the chance that family members will also read the patient information.

In one exemplary embodiment, the patient aid 500 has the esthetics of a greeting card, such as a "get well soon card" for example. It is understood that a greeting card is one way of presenting the first portion 501 of the patient aid 500 to induce a caregiver to present the "greeting card" to the patient. It is the outward appearance of the patient aid 500 in one embodiment, which is other than something that is generally related to the contents of the package it is carried in, which induces the caregiver to deliver the patient aid 500 to the proper recipient. Said differently, the greeting card appearance is configured to provide a caregiver a visual indicator that the patient aid 500 is intended for a patient. A greeting card look and feel thus forms one illustrative embodiment.

As noted above, the patient aid 500 does not necessarily have a greeting card look. For example, in another embodiment the patient aid 500 can be configured as a pediatric patient aid. In such a configuration, the picture 506 on patient aid 500 may include a caricature or cartoon character. This may be more appealing to children, and even some adults, than is the greeting card appearance. Medical procedure kits that may be used with children may include a patient aid that has carton characters and in one embodiment the character coincides with one or more current popular cartoon characters.

Figure 6:
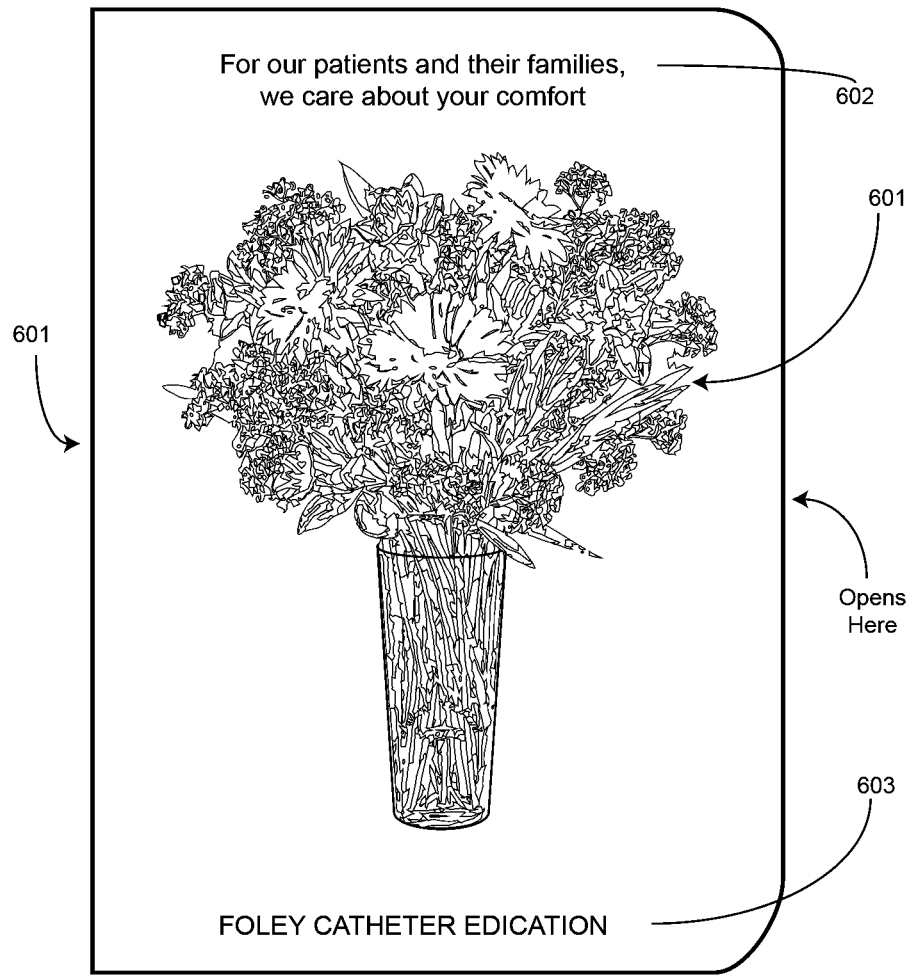
FIGS. 6-9 illustrate various examples of patient aids configured in accordance with one or more embodiments of the invention.

Turning now to FIG. 6, illustrated therein is one embodiment of a patient aid 600 with a first, outwardly facing portion configured as a greeting card. The patient aid 600 in this illustrative embodiment includes at least one healing color 604 and a greeting 605, which is configured in this embodiment as an inspirational phrase. Next, the outwardly facing portion includes an aesthetically pleasing image 606. The aesthetically pleasing image 606 of FIG. 6 is a depiction of a vase of flowers, although it will be clear to those of ordinary skill in the art having the benefit of this disclosure that embodiments of the invention are not so limited. Other aesthetically pleasing images include puppies, sunsets, mountain streams, and so forth. The bottom of the outwardly facing portion in this illustrative embodiment includes in identifier 607 that tells the patient the purpose of the patient aid 600.

As noted above, the inwardly facing portions can include patient information. For example, in one embodiment where the patient aid 600 is to be included with a catheter assembly, the interior includes the following illustrative text:

Here is some simple information about foley catheterization:

1. What is a Urinary Catheter?

A thin flexible tube that drains urine from the bladder into a collection bag. The catheter helps:

When you can't urinate.

To measure how much urine you're producing.

During and after some surgeries or tests.

2. What should you know about your catheter?

Only a trained technician inserts a catheter when necessary, and it is removed as soon as possible.

Caregivers must wash hands with soap or use alcohol-based rubs before and after touching your catheter.

If your caregivers don't clean their hands, politely ask them to.

Do not disconnect the catheter yourself.

Inquire every day whether you still need the catheter.

3. What is 'catheter-associated' urinary tract infection (CAUTI)?

If a catheter introduces 'outside' germs into your urinary tract, they can cause an invention. If a UTI is acquired, you may experience:

Sudden fever and/or bloody urine.

Burning or painful urination, or pain below the stomach.

Frequent, or more urgent, urinating after catheter is removed.

Tell your provider right away. An antibiotic may be needed.

4. Can you reduce your chances of an infection? Absolutely!

Wash your hands before and after touching your catheter.

Make sure the tube is secured to your leg. Never twist, or tug on it.

Always keep the collection bag below the level of your belly button.

Do not disconnect the catheter yourself.

Ask your doctor every day whether you still nee the catheter.

In accordance with the examples above, the patient information can include educational information corresponding to a medical procedure, patient care information corresponding to a medical procedure, information relating to a medical device applied to a patient, an illustrated guide depicting patient care for the medical device, instructions for patient-administered care, combinations thereof, or other medical educational information.

The illustrative information set forth above can be printed in multiple languages, such as in Spanish or in English. Where two languages are used, the back portion may be the same as the image shown in FIG. 6, but with the greeting 605 and optional identifier 607 being set forth in a different language. Further, alternatives and variations of the information can be substituted for the example set forth above.

Figure 7:
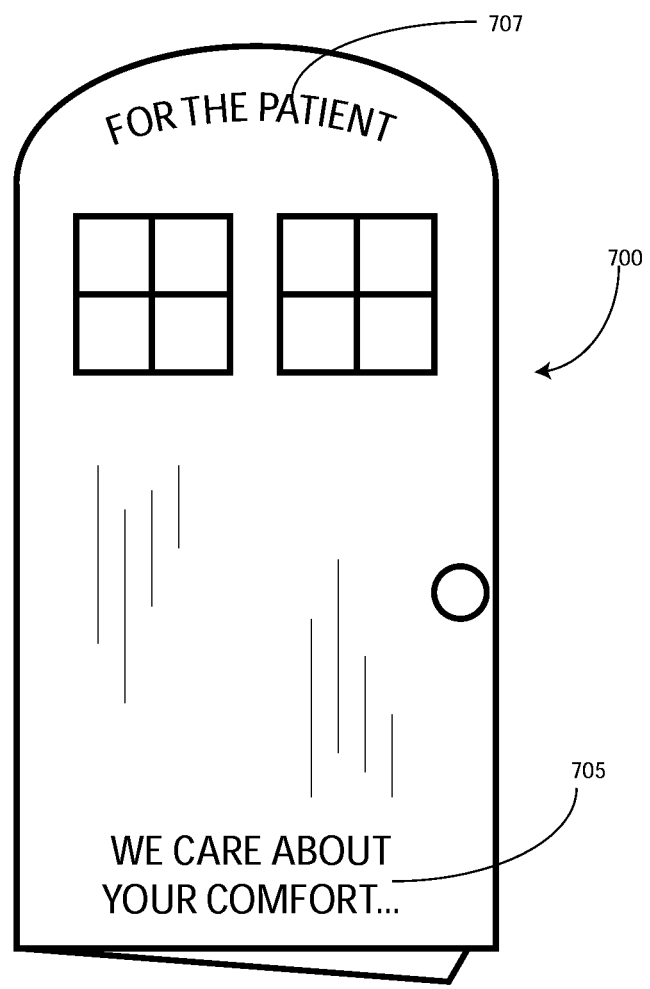
Figure 8:
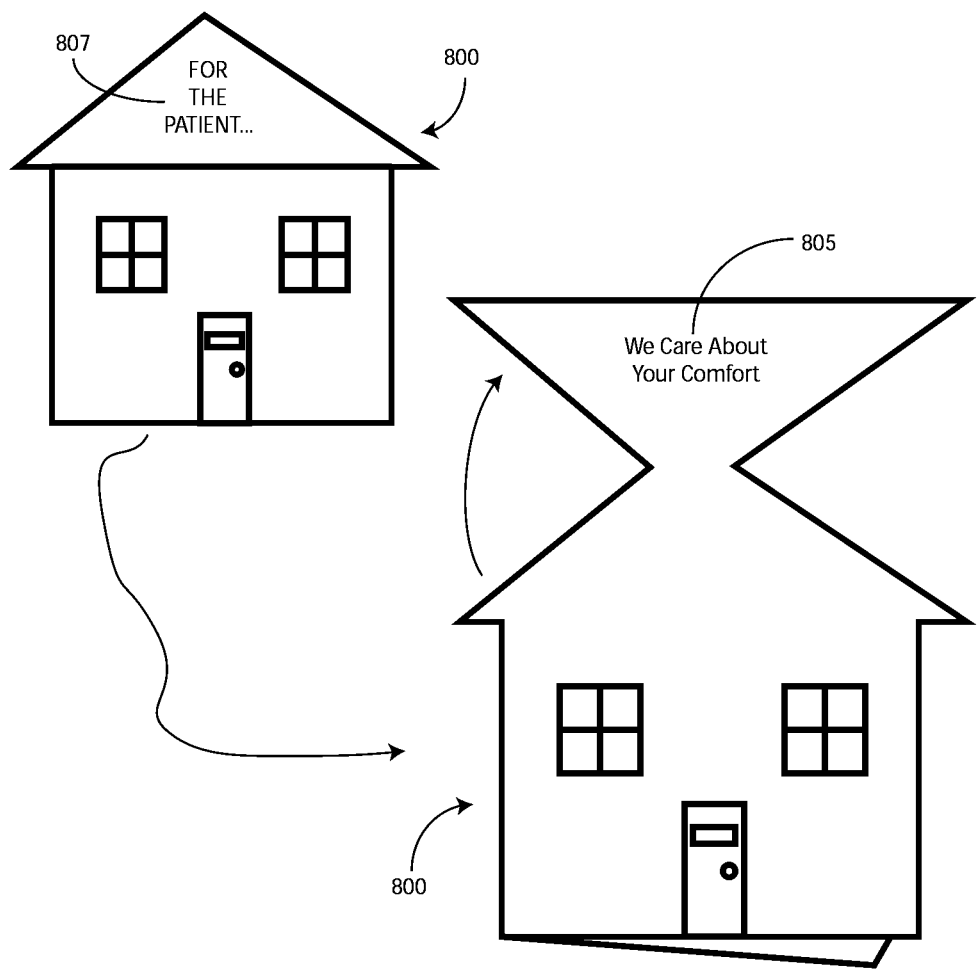

Turning now to FIGS. 7 and 8, illustrated therein are alternative types of patient aids 700,800 configured with greeting card appearances. Beginning with FIG. 7, the patient aid 700 has been die cut in the shape of a door. The door includes windows, a knob, and a wood grain paneling aesthetic. An identifier 707 configured to provide a caregiver a visual indicator that the patient educational card is intended for a patient is disposed at the top of the door, while a greeting 705 is disposed at the bottom of the door. When the patient opens the door, the patient educational information is found therein.

In FIG. 8, the patient aid 800 has been die cut in the form of a house. The house includes windows, a door, and a roof. The identifier 807 is disposed on the roof. The identifier 807 configured to provide a caregiver a visual indicator that the patient educational card is intended for a patient. When a patient opens the roof, the greeting 805 is revealed. When the patient opens the patient aid 800 by swinging an edge of the house from laterally across the front of the house, the patient educational information is found therein.

Figure 9:
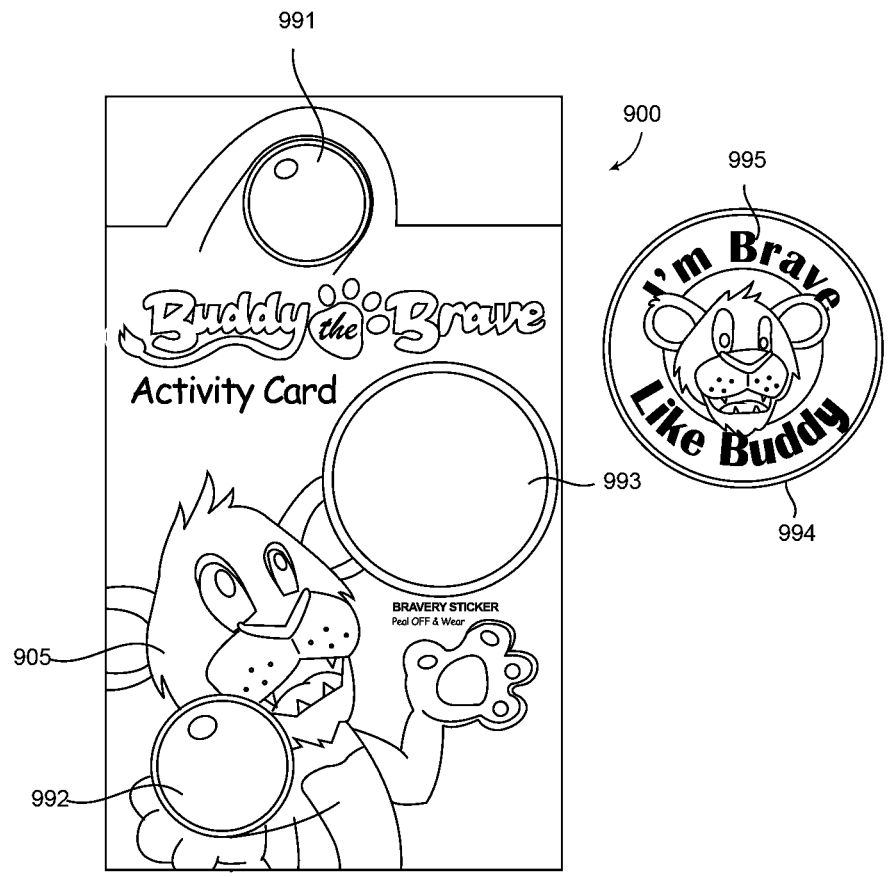

Turning now to FIG. 9, illustrated therein is a patient aid 900 configured as a pediatric patient aid. In this illustrative embodiment, the outwardly facing portion is configured as an activity card. The activity card of FIG. 9 comprises a cartoon 905, which in this case is a caricature of a young lion named "Buddy the Brave."

In one embodiment, the cartoon 905 defines an activity suitable for completion by a recipient. In the illustrative embodiment of FIG. 9, Buddy is shown juggling three balls 991,992,993. However, one of the balls 903 is shown as a blank. The activity card of this illustrative embodiment includes a sticker 994 suitable for attachment to the activity card. Accordingly, to give Buddy three balls to juggle, the activity defined by the cartoon 905 comprises attachment of the sticker 994 to the activity card.

To encourage patients to be brave, an inspirational phrase is disposed on one or both of the sticker 994 and the activity card. In this illustrative embodiment, the sticker 994 includes the inspirational phrase 995, which says, "I'm Brave Like Buddy," and this forms an indication that a recipient of the sticker is brave like a character depicted on the activity card. Either of the sticker 994 or activity card could correspondingly include a request to "be brave," such as "Be Brave Like Buddy," or "Can You Be as Brave as Buddy?" In this illustrative embodiment, the sticker 994, like the activity card, also includes a depiction of Buddy.

While a fanciful animal, Buddy, is shown in this illustrative embodiment, it will be clear to those of ordinary skill in the art having the benefit of this disclosure that embodiments of the invention are not so limited. The cartoon 905 or caricature could take other fanciful forms, including cartoon characters, super heroes, other animals, fanciful characters, and so forth. Additionally, the names, inspirational phrases, and other features could be different.

Figure 10:
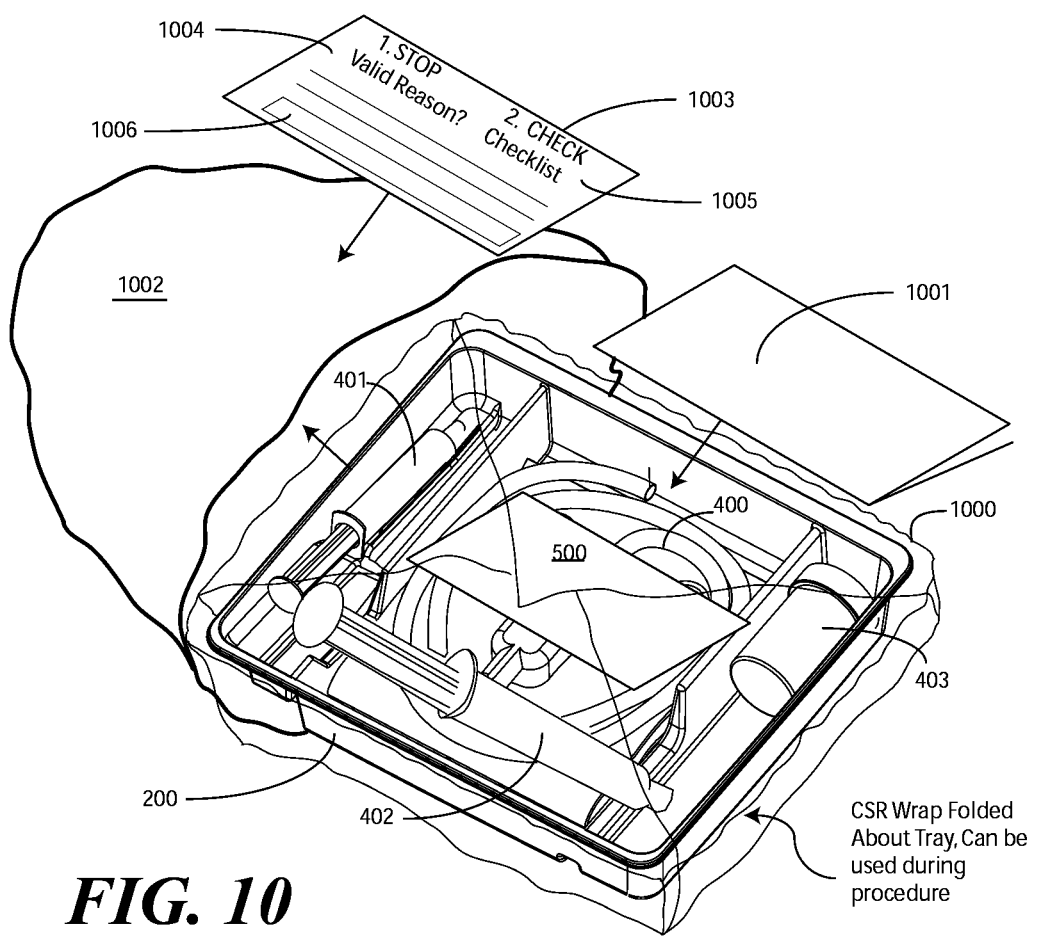
FIGS. 10-14 illustrate various examples of methods for packaging medical procedure kits in accordance with one or more embodiments of the invention.

Turning now to FIG. 10, illustrated therein is an illustrative packaging arrangement for a medical procedure kit configured in accordance with embodiments of the invention and including the tray 200 and assembly shown in FIG. 4 and the patient aid 500 of FIG. 5. FIG. 10 uses the catheterization procedure to illustrate how a patient aid 500 can be included with a medical procedure kit in accordance with one or more embodiments, although it is to be understood that other medical procedure kits configured for other procedures could be substituted for the catheterization kit shown.

FIG. 10 illustrates an exploded view of the tray 200 having the catheter assembly 400, a pair of syringes 401, 402, and a specimen container 403 disposed therein. While only a specimen container 403 is shown as being disposed in the third compartment, note that additional items could also be included within the third compartment, including swab sticks. Other devices could also be inserted into the tray 200 in various compartments as well. For example, in one embodiment, a catheter securement device, and a Foley insertion tag, which is a dated and/or time stamped label that is secured to the catheter tubing once the catheter is inserted, can be inserted into the second compartment. Also, note that the pair of syringes 401,402 can be configured as shown in FIG. 10, or alternatively can be both inserted in the first compartment, as described above. In the configuration of FIG. 10, rather than having both syringes 401,402 disposed within the first compartment, one syringe 402 is disposed laterally in the first opening and the second opening of the first barrier and second barrier, respectively. This configuration is illustrative only.

Once the necessary medical devices or components are disposed within the tray 200, the patient aid 500 can be disposed therein as well. In one embodiment, the patient aid 500 is disposed atop the medical devices. In one embodiment, the medical devices are arranged in order of use during a predefined medical procedure. It can be advantageous for the patient aid 500 to be disposed in a location that occurs early on in the procedure. When the patient aid 500 is disposed above the medical devices, it is arranged so as to be discoverable within three steps of the predefined medical procedure.

The patient aid 500 can include helpful suggestions or instructions for the patient. Examples of suggestions or instructions that may be included in the patient portion include information on what a catheter is, what the patient should understand about the catheter, how to reduce the chance of getting an infection, information about infections commonly associated with catheters, symptoms of infections commonly associated with catheters, and suggestions for home use of the catheter assembly.

Once the medical devices and patient aid 500 are disposed within the tray, the tray can be sealed with a wrap 1000 to keep the internal components sterile. The wrap 1000 can be any of a number of types of material. In one embodiment, the wrap 1000 comprises a Central Sterile Reprocessing (CSR) wrap that is used widely by medical professionals in hospitals, ambulatory surgical centers, and the like during medical procedures. While a CSR wrap is one example of a wrap that can be used, it will be clear to those of ordinary skill in the art that other wraps, such as plastic, cotton, linen, paper, or combinations thereof, can be substituted without departing from the spirit and scope of the invention.

Using a CSR wrap as an illustrative example, in one embodiment the CSR wrap 1000 is folded about the tray 200 for sealing, and can be correspondingly unfolded to reveal the tray 200. Once unfolded, the CSR wrap 1000 can then be used in the medical procedure. For example, an unfolded CSR wrap 1000 can be used to provide a sterile field in which the tray 200 sits for unloading and subsequent use.

Printed instructions 1001 intended for the health care services provider can then be attached to, disposed upon, or disposed within the tray 200. In one embodiment, the printed instructions 1001 inform the health care services provider how to use the kit. The health care services portion can include instructions telling the health care services provider, for example, how to set up a sterile or otherwise clean work environment, how to prepare the catheter assembly 400 disposed within the tray, how to use the other devices within the tray, how to insert the catheter, how to secure the drainage bag to the catheter, how to empty the drainage bag, how to obtain a urine sample, and so forth. The printed instructions 1001 instructions can include pictures or illustrations showing visually how the various steps should be done as well. In one embodiment, the printed instructions 1001 may include an instruction for the health care services provider to give the patient aid 500 to the patient and to discuss the information found in the patient aid 500 with the patient. In one embodiment, the printed instructions 1001 can notify the health care services provider that the devices disposed within the tray 200 are ordered corresponding to use during the medical procedure.

Once the patient aid 500 and printed instructions 1001 have been affixed to, or placed with, within, or atop the tray 200, the assembly can be sealed in packaging 1002 such as a thermally sealed bag. The thermally sealed bag can optionally include a preformed opening. For example, in one embodiment, the opening can include one or more tabs that a health care services provider is instructed to pull to open the bag.

Additional informational materials may be included with the completed assembly as well. For example, in one embodiment an adhesive instruction tag 1003 can be affixed to the packaging 1002. In one embodiment the instruction tag 1003 can include information regarding whether use of the medical procedure kit is even needed. With reference to a catheterization procedure, text 1004 such as "Is there a valid clinical reason?" may be included under an instruction to "Stop" that includes the following information:

Before inserting the Foley catheter, at least one of the following conditions should exist:
Acute urinary retention or obstruction
Precise measurement of urinary output needed
Select surgical procedures
Open sacral or perineal wounds in incontinent patient
Prolonged immobilization
End of life care Further, checklist text 1005 may be included, such as "Checklist for Foley Catheter Insertion" included under the word "Check" that includes the following information:
Check Each Box Upon Completion:
Obtain order from physician/provider
Document clinical reason for insertion
Explain procedure to patient
Use smallest catheter possible
Perform hand hygiene
Follow aseptic technique A fillable form 1006 can also be provided. The fillable form 1006 can provide fields for the date and time of insertion of the catheter to be recorded, the name of the health care services provider, and the signature of the health care services provider. The above text 1004 for the instruction tag 1003 is illustrative only, and may be customized as desired by the manufacturer.

Figure 11:
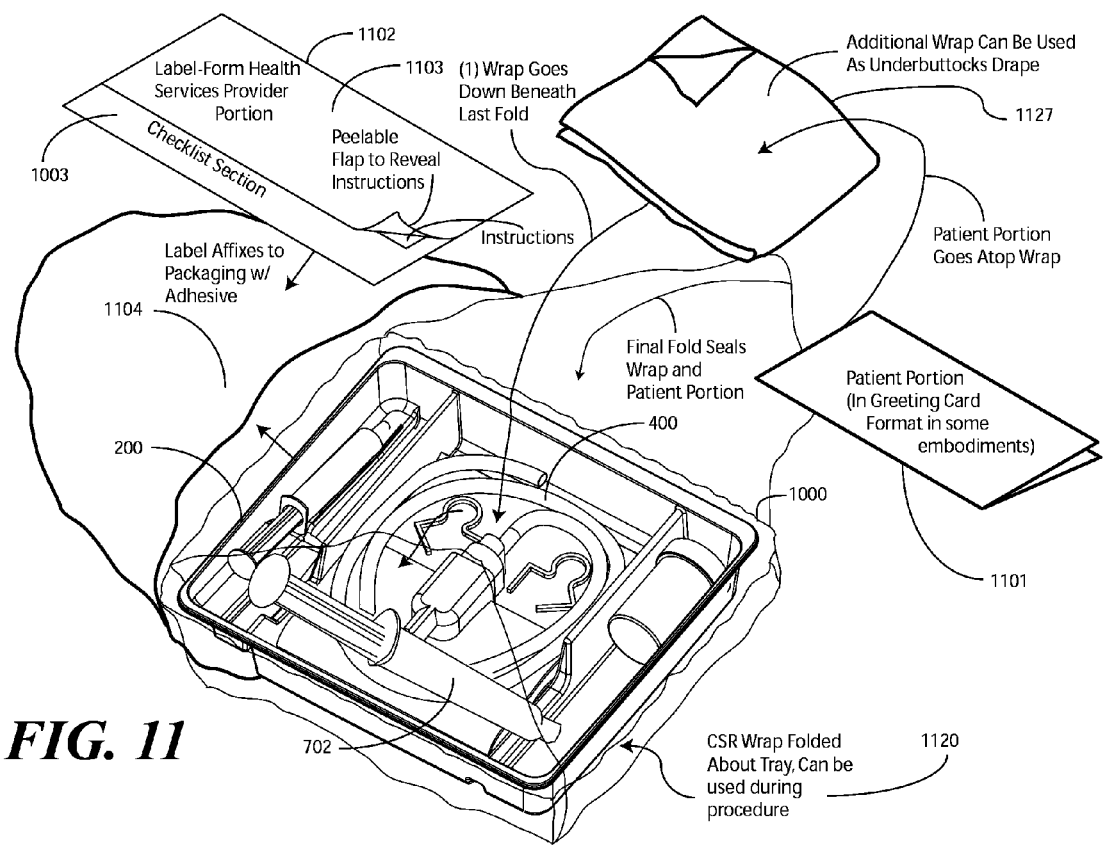
Figure 12:
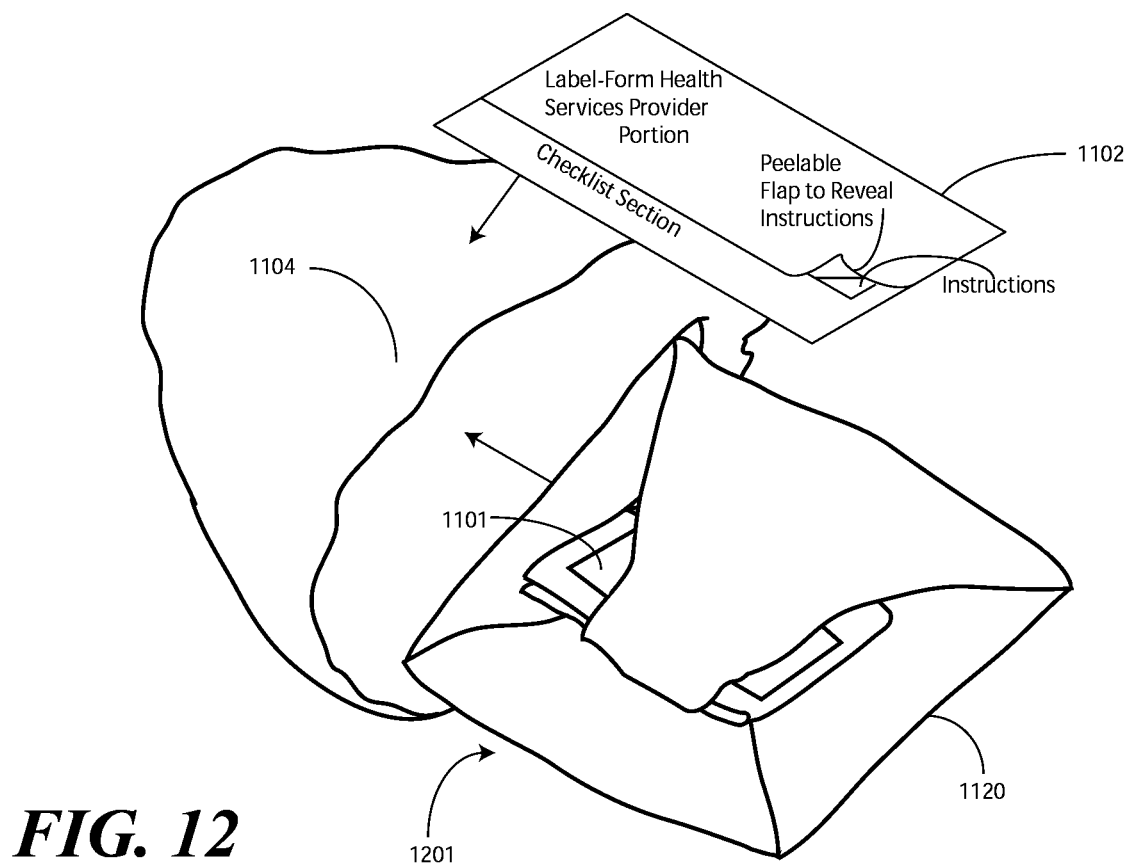

Turning now to FIGS. 11 and 12, illustrated therein is an alternate construction of a medical procedure kit configured in accordance with embodiments of the invention. In FIGS. 11 and 12, the printed instructions included with the medical procedure kit are physically separated into a patient aid 1101 and a health care services provider portion 1102. The patient aid 1101 can be configured with any number of aesthetically pleasing, entertaining, and/or comforting disguises, including that of the greeting card or activity card described above. In this particular embodiment, the health care services provider portion 1102 is configured as an adhesive label suitable for attachment on the outside of the packaging 1104. An instruction tag 1003, which can be similar to that described with reference to FIG. 10 above, can form an extension of the health care services provider portion 1102. In one embodiment, the health care services provider portion 1102 has a picture of the contents of the medical procedure kit on the top, and has a peelable flap 1103 that may be opened to reveal instructions and other indicia therein.

The patient aid 1101 can be configured with a disguise, which in this illustrative embodiment is a greeting card. Experimental testing has shown that when the patient portion is configured as an instruction or informational sheet, it is less likely that the patient portion will be delivered to the patient. For example, in some cases this information is stowed in the bottom of the overall package or the tray 200, or is mistakenly presumed to be "non-patient" information. In other cases, the material is simply forgotten about and thus does not make it to the patient. Testing has shown that with some health care service providers, once the device is applied, e.g., once the catheter of this example is placed, anything remaining in the packaging is presumed to be "trash" and is either not noticed or thrown away. However, by configuring the patient aid 1101 as a greeting card, such as with a pleasant picture of flowers or similar objects on the front and stylized text providing the information therein, it is more likely to be given to the patient. In one embodiment, the patient aid 1101 is configured as the patient aid (600) was in FIG. 6.

Once the necessary components are disposed within the tray 200, the tray 200 can be sealed or enclosed with a wrap 1000. The wrap 1000 can be thermally or adhesively sealed to the tray 200, or may alternatively be wrapped about the tray 200. The tray 200 may be sealed with a first wrap 1000, and then may have a folded layer of wrap material 1120 folded atop the first wrap 1000. Where the tray 200 is wrapped with a folded layer of wrap material 1120, CSR wrap can be used in one or more embodiments as the folded layer. Accordingly, a health care services provider can correspondingly unfold the CSR wrap to reveal the tray 200 and its contents. Once unfolded, the CSR wrap can be used as a component in the medical procedure. For example, an unfolded CSR wrap can be used to provide a sterile field in which the tray 200 sits for unloading and subsequent use.

As with some embodiments described above, the health care services provider portion 1102 can include instructions telling the health care services provider, for example, how to set up a sterile or otherwise clean work environment, how to prepare the catheter assembly 400 disposed within the tray 200, how to use the other devices within the tray 200, how to insert a catheter, how to secure a drainage bag to the catheter, how to empty a drainage bag, how to obtain a urine sample, and so forth. The instructions can include pictures or illustrations showing visually how the various steps should be done as well.

In one embodiment, the health care services provider portion 1102 can be configured as a booklet. For example, in one embodiment, the interior of the health care services provider portion 1102 can include one or more of the panels that will be shown in FIGS. 16-18 below. In one embodiment, the health care services provider portion 1102 may include an instruction for the health care services provider to give the patient aid 1101 to the patient, and in one embodiment, instructions to discuss the patient aid 1101 with the patient.

As with previous embodiments, the patient aid 1101 can include helpful suggestions or instructions for the patient. The patient aid 1101 can be configured as a greeting card to make the information more pleasantly received by a patient. Examples of suggestions or instructions that may be included in the patient portion include information on what a catheter is, what the patient should understand about the catheter, how to reduce the chance of getting an infection, information about infections commonly associated with catheters, symptoms of infections commonly associated with catheters, and suggestions for home use of the catheter assembly 400.

In the embodiment of FIG. 11, the patient aid 1101 is disposed within the packaging 1104, while the health care services provider portion 1102 is affixed to the outside of the packaging 1104. Where required for the medical procedure, additional layers of wrap material 1127 can be disposed within the packaging 1104. In one embodiment, the additional layers of wrap material 1127 can be configured to be visibly distinguishable from the wrap material 1120 disposed about the tray 200. For example, in one embodiment, the additional layers of wrap material 1127 are a different color than the one or more layers of wrap material 1120. In one or more embodiments, the additional layers of wrap material 1127 can be tucked within the folds of wrap material 1120. Other components may also be tucked within the folds of wrap material 1120, including packages of liquid hand sanitizer and packages of rubber gloves.

In FIG. 11, rather than being disposed within the tray 200, the patient aid 1101 can be placed atop the wrap material 1120. In one embodiment, the patient aid 1101 and any other external components such as the package of liquid hand sanitizer (where used), the rubber gloves (where used), and the additional layer of wrap material 1127 (where used), can be held in place by way of a final folding step occurring in the placement of wrap material 1120. The health care services provider will be readily able to access these implements after unfolding wrap material 1120.

The health care services provider portion 1102 can be adhesively affixed to the packaging 1104. The packaging 1104 can optionally include a preformed opening. For example, in one embodiment, the opening can include one or more tabs that a health care services provider is instructed to pull to open the packaging 1104.

Turning now to FIG. 12, illustrated therein is the medical procedure kit 1201 of FIG. 11 having the patient aid 1101 tucked-into the one or more layers of wrap material 1120. The health care services provider portion 1102 is affixed to the packaging 1104, which in one embodiment is a thermally or adhesively sealed bag.

Figure 13:
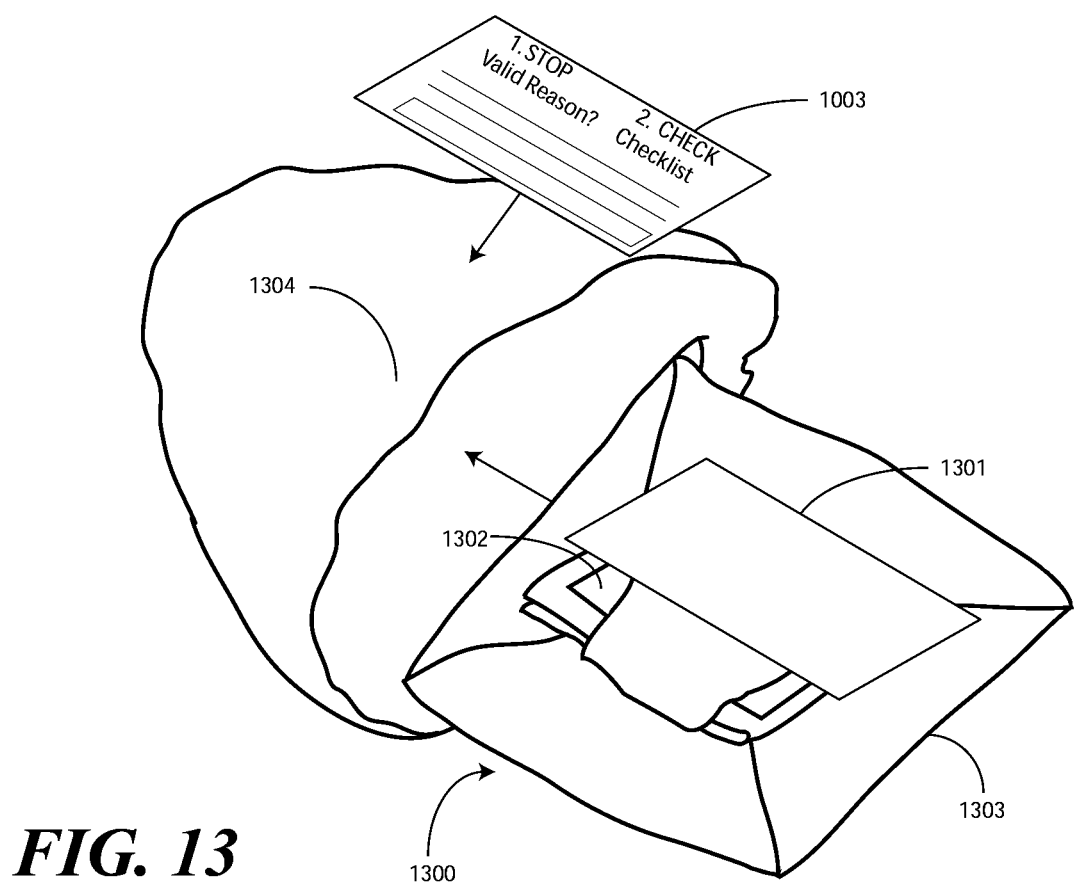

Turning to FIG. 13, illustrated therein is yet another medical procedure kit 1300 construction configured in accordance with one or more embodiments of the invention. In FIG. 13, the printed instructions for using the medical procedure kit include a health care services provider portion 1302 and a patient aid 1301, and each is physically separate from the other. The health care services provider portion 1302 is tucked-in to a folded wrap material 1303. The medical procedure kit 1300 is then sealed in a packaging material, which in this case is illustratively shown as a bag 1304. The patient aid 1301 is disposed atop the wrap material 1303.

Figure 14:
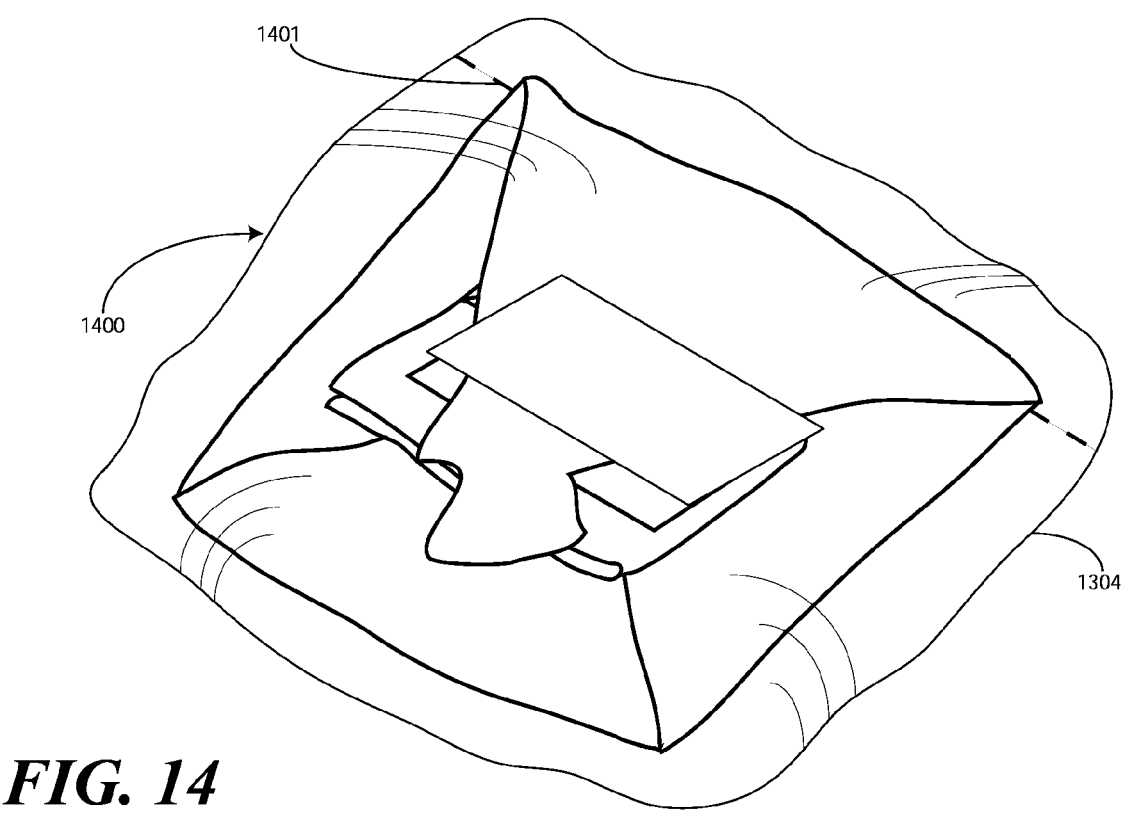

Once the printed instructions have been affixed to, placed with, placed atop, or disposed within the packaging, the packaging can be thermally or otherwise sealed. The completed assembly 1400 is shown in FIG. 14. The thermally sealed bag 1304 optionally includes a preformed opening 1401. For example, in one embodiment, the preformed opening 1401 can include one or more tabs that a health care services provider is instructed to pull to open the bag 1304.

Figure 15:
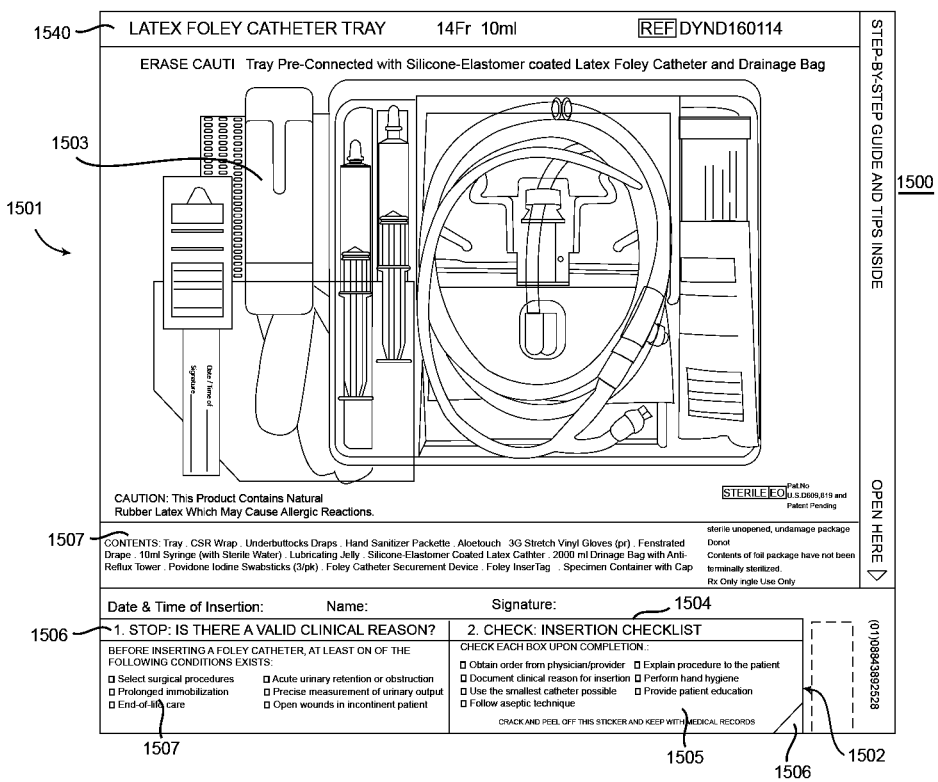
FIGS. 15-18 illustrate examples of health care services provider information suitable for inclusion with printed instructions in medical procedure kits configured in accordance with one or more embodiments of the invention.

Turning now to FIG. 15, illustrated therein is one example of a health care services provider portion that is suitable for inclusion with a medical procedure kit. The illustrative health care services provider portion of FIG. 15 is configured as a printed label 1501, and accordingly is suitable for use as the health care services provider portion (1102) of FIG. 11. However, it will be clear to those of ordinary skill in the art having the benefit of this disclosure that the content shown in FIG. 15 could equally be used in the printed instructions (1001) described in FIG. 10.

The printed label 1501 of FIG. 15 includes a peelable label 1502. As will be shown in subsequent figures, the peelable label 1502 is separable from the printed label 1501. In the illustrative embodiment of FIG. 15, the peelable label 1502 is separable from the printed label 1501 such that the peelable label 1502 may be removed and attached to medical records while the printed label 1501 stays affixed to outer packaging or an outer wrap of a medical procedure kit.

In one embodiment, the peelable label 1502 includes a red banner 1506 and one or more yellow panels 1507. The red banner 1506 is configured as a warning label. The one or more yellow panels 1507 are configured with checkable boxes corresponding to elements associated with the warning on the red banner 1506.

In the illustrative embodiment of FIG. 15, the printed instructions 1500 are configured for use with a catheter tray assembly. Accordingly, the red banner 1506 includes information relating to usage of a catheter assembly. The warning message in FIG. 15 includes information questioning whether there is a valid reason for using the catheter tray assembly. Specifically, this information recites the warning "Stop," followed by the question "Is there a valid clinical reason [for using the catheter assembly]?"

Beneath this warning, on one of the yellow panels 1507, are disposed a plurality of medical conditions that, where present, would provide a reason for using the catheter tray assembly. Each of these medical conditions has a white, markable square thereby. In this illustrative embodiment, the medical conditions read "Select surgical procedures," "Prolonged immobilization," "End-of-life care," "Acute urinary retention or obstruction," "Precise measurement of urinary output," and "Open wounds in incontinent patient." These conditions are illustrative only, as others will be readily apparent to those of ordinary skill in the art having the benefit of this disclosure. Further, the conditions in the illustrative embodiment of FIG. 15 correspond to catheter use. Where the medical procedure kit is something other than a catheter kit, other conditions will be more appropriate for listing in the yellow panel 1507.

By providing the white, markable squares, a medical services provider is able to mark with a pen or pencil which condition justifies the use of the medical procedure kit. As noted above, in one embodiment, the peelable label 1502 is configured for detachment from the printed label 1501 and attachment to medical records. Accordingly, the white, markable squares permit a nurse, doctor, or other medical services provider to create procedure-specific medical records without the need of obtaining specialized forms.

The choice of color in some applications can be important. For, example, the peelable label 1502 of FIG. 15 includes a red banner 1506 set against one or more yellow panels 1507. Experimental testing has shown that this particular color combination works as an "attention getter" for medical professionals in that they easily recognize this color combination. Further, the use of red serves as a mnemonic that a warning is present. Experimental testing has shown that the color yellow works as a mnemonic for a to-do list. The use of white for the markable squares works to make them easily identifiable. Further, markings therein are easily visible and capable of photocopying where necessary without degrading the medical service provider's writing.

In addition to the warning, in this embodiment the red banner 1506 also includes information 1504 indicating that a checklist corresponding to the use of the medical procedure kit is provided. In this illustrative embodiment, the information 1504 corresponds to the use of a catheter, and reads "Check: Insertion Checklist."

Beneath the information on one of the yellow panels 1507 and configured in black text, is a checklist configured to permit a medical services provider to check-off steps of completion when using the catheter assembly. In this illustrative embodiment, the steps include "Obtain order form from physician/provider," "Document clinical reason for insertion," "Use the smallest catheter possible," "Follow aseptic technique," "Explain procedure to the patient," "Perform hand hygiene," and "Provide patient education." These steps are illustrative only, as others will be readily apparent to those of ordinary skill in the art having the benefit of this disclosure. Further, the steps of the illustrative embodiment of FIG. 15 correspond to catheter use. Where the medical procedure kit is something other than a catheter kit, other steps will be more appropriate for listing in the yellow panel 1507.

As with the medical conditions, each of the steps is provided with a white, markable square thereby. As noted above, by providing the white, markable squares, a medical services provider is able to mark with a pen or pencil which steps were completed so that a physician or other person may review the steps at a later time. Where the peelable label 1502 is configured for detachment from the printed label 1501 and attachment to medical records, the white, markable squares permit a nurse, doctor, or other medical services provider to create procedure-specific medical records without the need of obtaining specialized forms. In the illustrative embodiment of FIG. 15, the peelable label 1502 includes red text 1505 indicating that the peelable label 1502 is configured for attachment to corresponding medical records. Further, a red symbol 1506 indicating a location at which a user can peel the peelable label 1502.

Disposed atop the peelable label 1502 is the printed label 1501. As will be shown below, in one embodiment the printed label 1501 can be configured as a booklet with at least one page that is configured to be peeled away from at least another page to reveal pictorial, step-by-step instructions for using the medical procedure kit.

As shown in FIG. 15, an outer page of the printed label 1501 includes a color photograph 1503 of the medical assembly disposed within the kit. The color photograph 1503 is disposed on a panel beneath a colored banner 1540 comprising a description of the medical assembly. In the illustrative embodiment of FIG. 15, the colored banner 1540 is either purple or blue, while the panel is black to emphasize the contents shown in the color photograph 1503. Additionally, a textual listing 1507 of the medical assembly and corresponding implements disposed within the medical procedure kit is provided in the black panel.

When the printed label 1501 is configured as a booklet comprising at least one peelable flap that, when opened, reveals instructional material corresponding to usage of the medical kit therein, at least one page can be configured to be longer than at least another page so as to have a portion 1505 extending beyond the at least another page so as to be visible when the booklet is closed. In the illustrative embodiment of FIG. 15, a bottom page extends beyond the top page having the color photograph 1503 disposed thereon, so as to reveal the portion 1505. In one embodiment, the portion 1505 is configured to be yellow so as to be set off from the black panel disposed beneath the color photograph 1503. Further, in one illustrative embodiment, the portion 1505 comprises an indication instructional material is disposed within the booklet.

Figure 16:
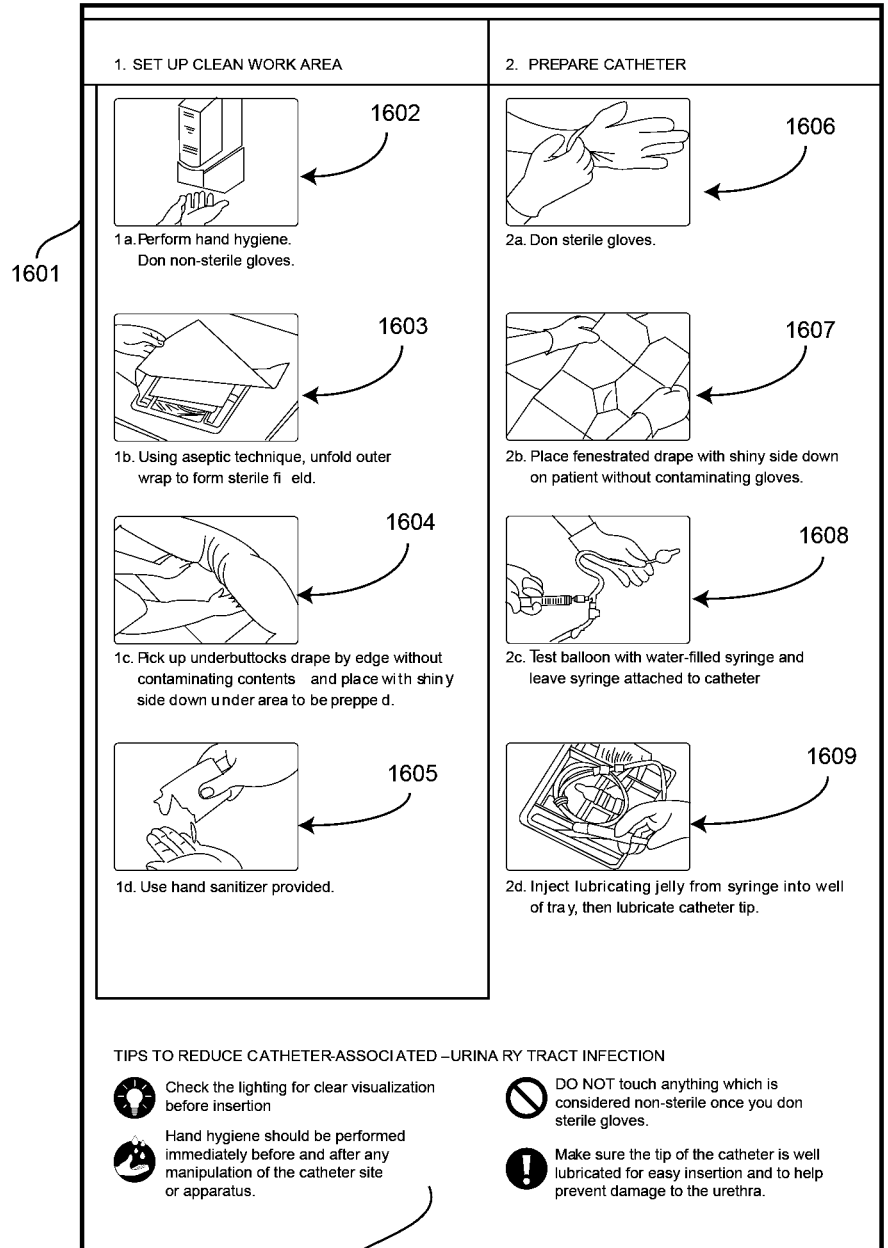
Figure 17:
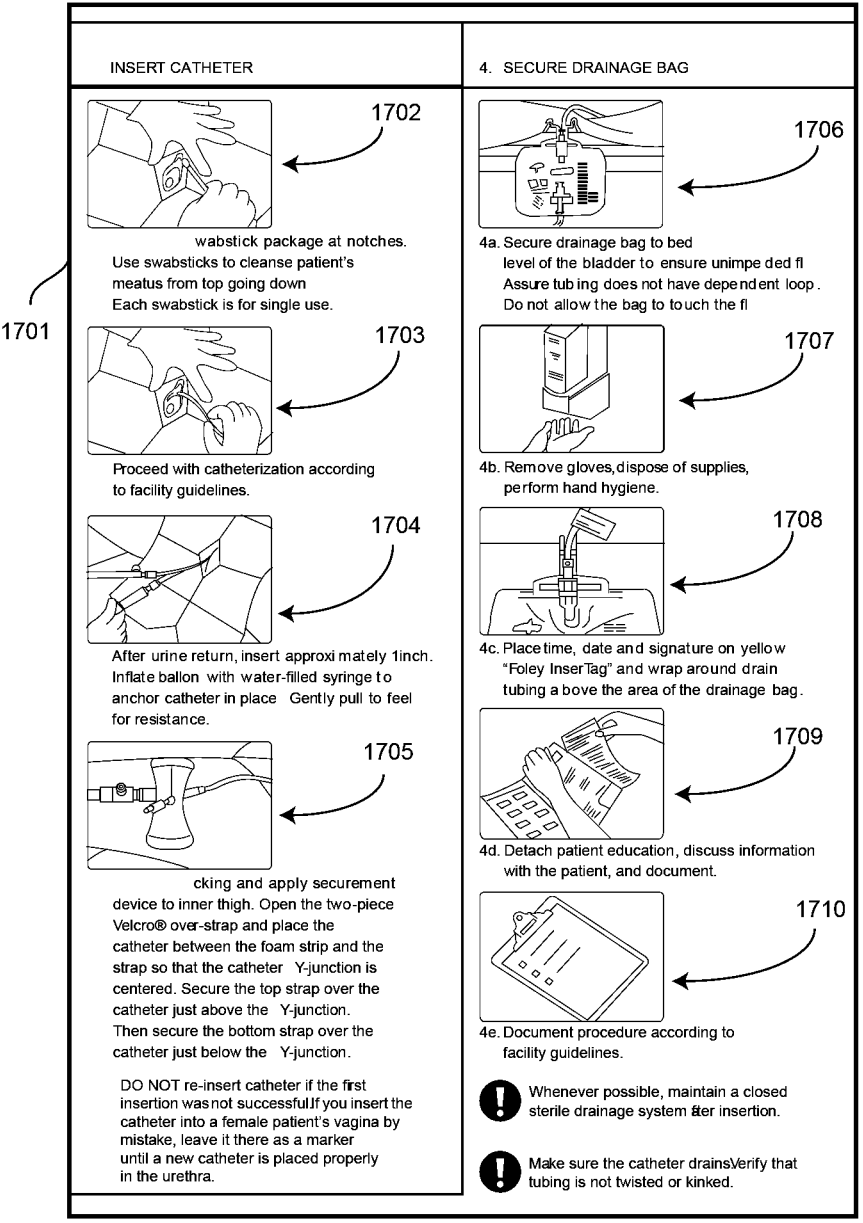
Figure 18:
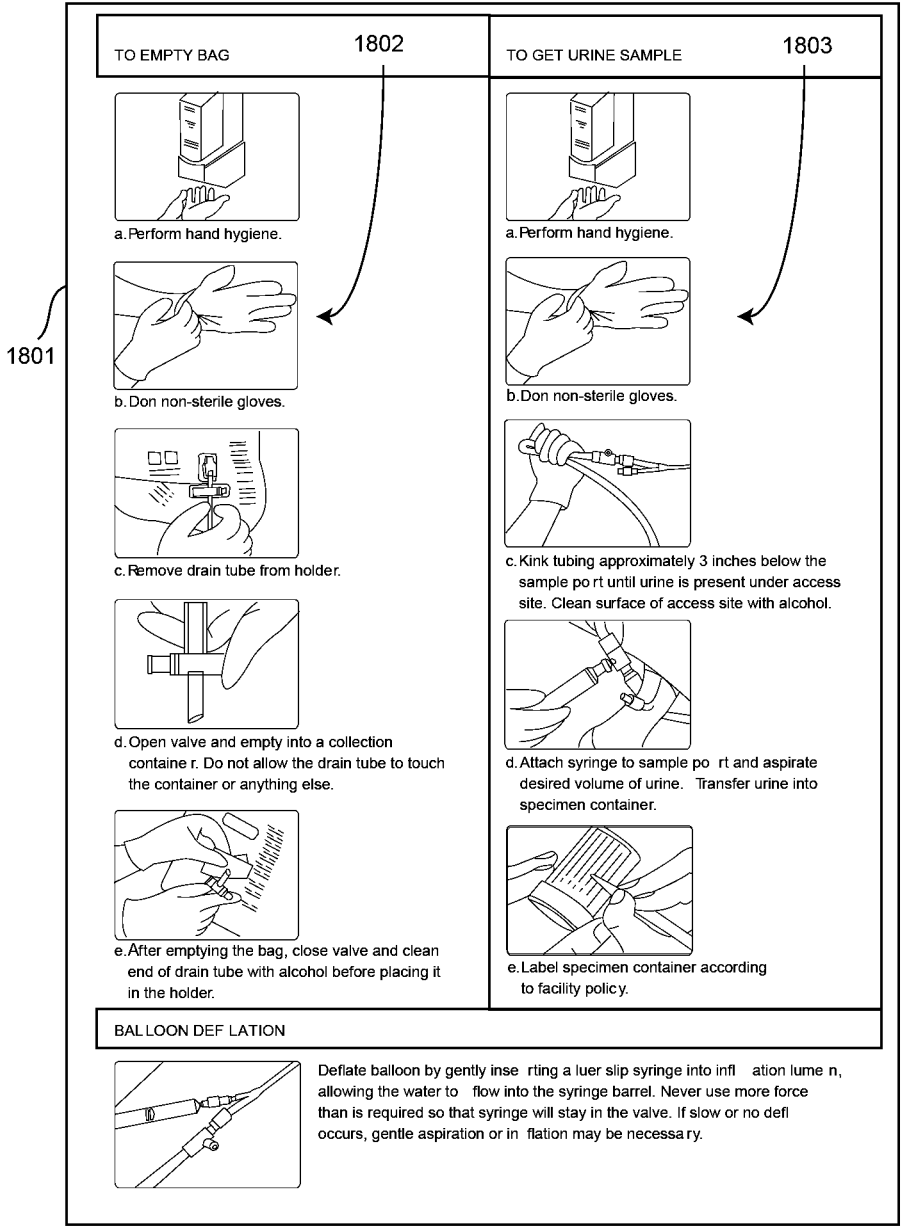

In the illustrative embodiment of FIG. 15, this indication is configured as black text disposed atop a yellow banner. The portion 1505 works to identify the printed label 1501 as being a booklet, and further provides notice that more information is located within the printed instructions 1500. The additional information can be accessed by the peelable flap. Examples of the additional information that can be located in the printed instructions 1500, in the illustrative catheterization application, are shown in FIGS. 16-18. In one embodiment, the information is configured as pictorial steps arranged in a plurality of columns, with adjacent columns have different colors.

Turning to FIG. 16, illustrated therein is one embodiment of a page 1601 suitable for inclusion with health care services provider instructions when the medical procedure kit is a catheterization kit. Page 1601 can include instructions for using the catheter assembly and the corresponding medical devices. Page 1601 can include instructions for setting up a clean work area. The instructions can include text, pictures, illustrations, or combinations of these.

In one embodiment, the instructions for setting up a clean work area include a hygiene performance step 1602, which may include instructions to wash hands, optionally put on gloves (which at this step can be non-sterile gloves), and so forth. The instructions may then include information on opening the remainder of the catheter package assembly. For instance, in FIG. 16 step 1603 indicates that the health care provider should remove the CSR wrap, which in this case is folded about the tray. As the CSR wrap is folded about the tray, removal of the CSR wrap by unfolding provides a sterile field about the tray.

Step 1604 then instructs the health care provide to pick up the underbuttocks of the patient and to place the underbuttocks wrap beneath the patient. Step 1605 then instructs the health care provider to use the hand sanitizing solution provided with the catheter package assembly. Page 1601 may include suggestions 1510 for preventing a catheter associated urinary tract infection.

In addition to information for setting up a clean work area, in one embodiment page 1601 includes instructions for preparing the catheter assembly as well. For example, step 1606 instructs the health care services provider to don sterile gloves, as the hands were sanitized at step 1605. Step 1607 tells the health care services provider to place the fenestrated drape with a shiny side down on the patient without contaminating the sterile gloves donned at step 1606. Step 1608 instructs the health care services provider to test the balloon of the catheter assembly with the water-filled syringe stored in the first compartment. Step 1608 also instructs the health care services provider to leave the syringe connected to the catheter assembly.

Step 1609 then provides instructions on using the first compartment of the tray as a lubricant application chamber as described above. Specifically, in this illustrative embodiment, step 1609 instructs the health care services provider to inject the lubricating jelly found in the second syringe of the first compartment into the first compartment. Step 1609 also instructs the health care services provider to pass the tip of the catheter through the first opening in the wall separating the first compartment and second compartment into the lubricating jelly, thereby lubricating the tip of the catheter.

Turning now to FIG. 17, illustrated therein is another exemplary page 1701 of health care services provider instructions. The instructions printed thereon continue to provide the health care services provider with information regarding use of the catheter assembly. For example, in one embodiment, this information includes instructions on inserting the catheter.

At step 1702, the instructions direct the health care services provider to tear open the swab stick package and to use the swab sticks to clean the patient from the top down. The instruction also notes that each swab stick is intended for one use only to properly maintain the sterile field. Step 1703 directs the health care services provider to initiate the catheterization process by inserting the catheter assembly into the patient. Steps 1704 and 1705 continue this process.

Step 1706 directs the health care services provider to secure the drainage bag to the catheter assembly. Step 1707 directs the health care services provider to clean up upon completion of the catheterization process. Step 1708 provides instructions on completing the label on the Foley insertion tag included with the catheter package assembly and attaching it to the tubing or drain bag attached to the catheter assembly.

At step 1709, the health care services provider is instructed to remember to deliver the patient aid to the patient. Step 1710 further instructs the health care services provider to discuss the patient information printed upon the patient aid with the patient. Step 1710 instructs that documentation of the entire procedure should be completed.

Turning now to FIG. 18, illustrated therein is another page 1801. Page 1801 provides information 1802 for emptying the drain bag and information 1803 describing how to obtain a urine sample can be included.

Turning now to FIGS. 19 and 20, illustrated therein are examples of patient information suitable for inclusion with any of the previously described patient aids. Recall from above that a disguise can be placed on a first portion of a patient aid, with patient information disposed on a second portion of the patient aid. FIGS. 19 and 20 include information suitable for placement on the second portion, again using a catheter procedure as an illustrative example.

Beginning with FIG. 19, the patient information can include information 1901 describing what a catheter is and why a catheter might be used. It also can include information 1902 describing what the patient should know regarding catheters and catheter use. For example, this information 1902 might notify the patient that the health care services provider should wash hands prior to inserting the catheter, and that it is acceptable to ask them to do so if they have not done so before the patient.

The patient information can also include information 1903 regarding how the patient can reduce the chances of getting an infection. This information 1903 can include a statement that the patient should wash their hands prior to touching the catheter assembly. The information 1903 may also include a statement that the drainage bag should always be kept at a level beneath the patient's navel, and that the patient should inform a helper when the bag is more than half full.

Turning to FIG. 20, additional patient information is shown. The additional information provides information that a patient may wish to know when using a catheter assembly. By way of example, information 2001 informs the patient as to what common infections associated with catheter use are and how they are contracted. Information 2002 provides symptoms of these common infections, such as fever, blood in the urine, burning or painful urination, or frequent or more urgent urination after catheter removal. Information 2003 informs the patient of what they should know prior to going home after a catheter procedure.

Information 2004 comprises an informational section configured such that a health care provider's name and contact information may be written thereon. This is helpful to the patient in the event that the symptoms recited in information 2002 should arise after the procedure, in that the patient has readily available access to the information required to contact a physician or other health care provider. An advantage of having this information 2004 on the patient aid is that the patient can take it with them upon completion of the procedure.

Turning now to FIG. 21, illustrated therein is an example of a set 2101 of information suitable for inclusion with a pediatric patient aid. The information has largely the same content as that found in FIGS. 19 and 20. However, it is different in that it is configured as "family information" since the patient will be a pediatric patient. Exemplary text is set forth here:

What you should know about your child's catheter.
1. What is a Urinary Catheter?
A thin flexible tube that drains urine from the bladder into a collection bag. The catheter helps:
When your child can't urinate.
To measure how much urine the child is producing.
During and after some surgeries or tests.
2. What to know about your child's catheter?
Only a trained technician inserts a catheter when necessary, and it is removed as soon as possible.
Caregivers must wash hands with soap or use alcohol-based rubs before and after touching your catheter.
If your caregivers don't clean their hands, politely ask them to.
Do not remove or disconnect the catheter yourself and remind the child not to touch the catheter.
Ask your caregiver often whether the child still needs the catheter.
3. What is 'catheter-associated' urinary tract infection (CAUTI)?
If a catheter introduces 'outside' germs into your urinary tract, they can cause an invention. If a UTI is acquired, you may experience:
Sudden fever and/or bloody urine.
Burning or painful urination, or pain below the stomach.
Frequent, or more urgent, urinating after catheter is removed.
Tell your provider right away. An antibiotic may be needed.
4. Can you reduce your chances of UTIs? Yes!
Wash hands (yours, the caregiver's, and the child's) before and after touching your catheter.
Make sure the tube stays secured to the child's leg.
Make sure the collection bag stays below the level of the child's belly button and off the floor.
Do not remove or disconnect the catheter yourself; only the trained caregiver, nurse, or doctor should do this.
Ask daily whether the catheter is still needed.

Turning now to FIG. 22, illustrated therein is a printed label 2201 configured for attachment to, or inclusion with, a pediatric medical procedure kit. The label 2201 is substantively similar to the one shown in FIG. 15. Accordingly, the common elements will not be repeated. The label 2201 is suitable for use as health care services provider information in a medical procedure kit.

The label 2201 differs from that of FIG. 15 because it includes an indication that the medical procedure kit is intended for pediatric use. In the illustrative embodiment of FIG. 22, the label 2201 includes a caricature 2202 indicating that the medical procedure kit is intended for pediatric use and includes pediatric patient educational material. The illustrative label 2201 further comprises indicia 2203 instructing a user to look inside the medical procedure kit for the pediatric patient educational material.

The caricature 2202 shown in FIG. 22, and in more detail in FIG. 23, is a fanciful animal. In particular, the caricature 2202 is a lion named "Buddy the Brave." Buddy, in this illustrative embodiment, is depicted as tearing through the printed label. As noted above, the caricature 2202 could take other forms, such as other animals, cartoon characters, super heroes, fanciful figures, and so forth. In a generic embodiment, the caricature 2202 comprises a fanciful character, such as a cartoon animal, and encouragement indicia.

As shown in FIG. 22, the caricature 2202 of Buddy is configured as a cartoon indicating that the medical procedure kit is intended for pediatric use and includes pediatric patient educational material. Both Buddy and his name are shown on the label 2201. Buddy's full name, "Buddy the Brave," comprises encouragement indicia in the form of a request to "be brave" like Buddy, as indicated by his last name. The label 2201 further includes indicia 2203 instructing a user to look inside the medical procedure kit for the pediatric patient educational material.

As with FIG. 15, the label 2201 is configured as a booklet comprising at least one peelable flap 2204 that, when opened, reveals instructional material corresponding to usage of the medical procedure kit. In this illustrative embodiment, the booklet comprises at least one page 2205 that is longer than at least another page 2206 so as to have a portion of page 2205 that extends beyond page 2206 so as to be visible when the booklet is closed.

In one embodiment, suitable for use with either the label of FIG. 15 or the label 2201 of FIG. 22, the booklet comprises pressure sensitive adhesive 2207 disposed between pages of the booklet. In one embodiment, the pressure sensitive adhesive 2207 is configured to make an audible sound when the pages 2205,2206 are peeled apart. Experimental testing has shown that instructing health care services providers to "remember to give the patient aid to the patient when you hear the peeling sound" are successful in getting the health care services provider to more frequently deliver the patient aid to the patient. Accordingly, in one embodiment, the audible sound is configured as a mnemonic reminder of the patient aid being disposed within the medical procedure kit. The audible sound also serves as a mnemonic reminder that the patient aid disposed within the medical procedure kit should be delivered to a patient.

Turning now to FIG. 23, a health care services provider 2303 is away page 2205. The pressure sensitive adhesive 2207 disposed between the pages gives way and makes a "CSHHHHHKKKK" sound, thereby providing the health care services provider 2303 with the mnemonic device to provide the patient portion disposed within the medical procedure kit to the patient.

The revealed instructional material 2301 comprises pictorial, step-by-step instructions for using the medical procedure kit. In this illustrative embodiment, the instructional material 2301 is presented in a colored, columnar format. The columnar format includes four columns, with each column including a heading banner indicating a concept to which the pictorial steps below relate. Experimental testing has shown that such a columnar format is highly successful in quickly and accurately delivering the series of steps to a medical services provider. In this illustrative embodiment, the columnar format employs alternating colors. The illustrative colors of this example are blue and white. It is contemplated that the blue color can be substituted with green or grey as well. In one embodiment, to provide a continuous audible sound while the pages are being opened, the pressure sensitive adhesive 2207 can be disposed at least substantially along a longitudinal length of the pages. In such an embodiment, the pressure sensitive adhesive 2207 could be disposed across an entire area of the page, or alternatively can be applied in a strip across a portion of the page extending the longitudinal length. Accordingly, when the pages are peeled open, the audible sound is generated substantially from start to finish of the peel back action.

The heading banners alternate color as well in this illustrative embodiment. For instance, blue columns have black heading banners, while white columns have blue heading banners. Where grey or green is substituted for blue, white columns may have grey or green heading banners. Segments relating to the prevention of injury or infection in the patient can be given a higher priority and a differently colored heading banner, such as red.

Turning now to FIG. 24, illustrated therein is a method 2400 for assembling a medical procedure kit configured in accordance with embodiments of the invention. The method 2400 can be carried out with the assistance of machines, such as automated assemblers, conveyer belt machines, robotic components, and so forth.

At step 2401, a manufacturer or assembler provides packaging, such as the tray shown in FIGS. 1 and 2. Once the tray or other packaging is procured, the manufacturer or assembler can dispose at least medical device in the tray at step 2402. Optionally, at step 2403, the manufacturer may arrange the medical devices according to order of use in a particular medical procedure.

At step 2404, the manufacturer or assembler disposes a patient aid within the tray or container. Where the medical procedure kit is a pediatric kit, step 2404 can include disposing a pediatric patient aid within the tray, wherein the pediatric patient aid includes patient information disposed on a first portion of the pediatric patient aid and an activity card or other disguise disposed on a second portion of the pediatric patient aid. In another embodiment, step 2404 can include disposing a patient aid within the tray, the patient aid comprising a set of patient information carried on an inner portion of the patient aid and a greeting card appearance disposed on an outward facing portion of the patient aid. At step 2407, the medical tray assembly can be enclosed in packaging material.

Where the medical devices are arranged in a predetermined sequence corresponding to order of use in a medical procedure at step 2403, step 2404 can include arranging the patient aid at a location corresponding to a particular step in the predetermined sequence. For example, in one embodiment, to avoid the "everything remaining is trash" issue identified above, it is desirable to dispose the pediatric patient aid at a location corresponding to one of three first steps occurring in the predetermined sequence at step 2404. In another embodiment, step 2404 can comprise disposing the patient aid atop the medical devices so that it is the first thing seen when any outer wrapping is removed. In another embodiment, step 2404 can come after the tray or packaging is wrapped at optional step 2405 such that the patient aid is disposed atop interior wrapping but within the packaging material as described above with reference to FIG. 14.

Health care services provider information is included at step 2406. In one embodiment, the health care services provider information is placed within the tray or other enclosure. In another embodiment, the health care services provider information is included outside the wrap applied at optional step 2405, but within the packaging applied at step 2407. In yet another embodiment, the health care services provider information is applied as a label to the packaging applied at step 2407.

Where a label is used, the label can comprise a booklet having pressure sensitive adhesive disposed between pages of the booklet, the pressure sensitive adhesive being configured to create an audible sound when the pages are opened. Where such a mnemonic device is employed, the manufacturer or assembler may, and possibly with the assistance of a computer or other communication device, instruct health care services providers to remember to deliver the patient aid disposed within the medical procedure kit to the patient at step 2408. At step 2409, the completed assembly can be shipped to a medical services provider.

Turning to FIG. 25, illustrated therein is one method 2500 of using a medical procedure kit configured in accordance with one or more embodiments of the invention. The method 2500 results is transformative as it transforms a patient from an untreated physical condition to a condition of having received treatment and/or having been attached to a medical device in accordance with the procedure corresponding to the medical procedure kit.

At step 2501, the health care services provider opens any packaging disposed about the medical procedure kit. In one embodiment, the medical procedure kit has therein one or more medical devices and a patient aid comprising a set of patient information disposed on a first portion of the pediatric patient aid and a disguise disposed on a second portion of the pediatric patient aid. Where the medical procedure kit is a pediatric kit, the patient aid can be configured as a pediatric patient aid, where the pediatric patient aid includes patient information disposed on a first portion of the pediatric patient aid and an activity card or other disguise disposed on a second portion of the pediatric patient aid. In another embodiment, the patient aid can be configured as a greeting card with a set of patient information carried on an inner portion of the patient aid and a greeting card appearance disposed on an outward facing portion of the patient aid.

In one embodiment, the medical procedure kit comprises both the patient aid and health care services provider information. At step 2502, the health care services provider information is accessed. In one embodiment, this includes removing the information from the medical procedure kit. In another embodiment, the health care services provider information is configured as a label attached to the outer packaging. In one embodiment, the label is configured as a booklet. In one embodiment, the booklet includes pressure sensitive adhesive configured to make an audible noise when the pages of the booklet are opened. As described above, this can be used as a mnemonic device to remember to give the patient aid to the patient. Where this latter embodiment is used, optional step 2503 comprises opening the booklet and hearing the audible noise. Optional step 2504 includes identifying the mnemonic device and remembering to deliver the patient aid, obtained at step 2505, to the patient at step 2507.

Where the audible mnemonic device is not employed, identification of the patient aid can be accomplished by other means at step 2506. For example, as noted above, in one embodiment the medical devices placed within the medical procedure kit are arranged in a predetermined order of use. Further, the patient aid is disposed at a predetermined step, such as within the first three steps of the procedure. Accordingly, the patient aid is identified at step 2506 by performing the medical procedure in accordance with its predetermined steps.

In other embodiments, the label or other printed instructions may include indicia indicating that a patient aid is included. For example, where the medical procedure kit is configured as a pediatric patient kit, a cartoon or caricature or other indicia may be present on a label indicating that the medical procedure kit includes the patient aid. Accordingly, the patient aid can be identified at step 2506 by noticing the cartoon, caricature, or other indicia. Once the patient aid has been delivered to, and discussed with, the patient, the medical procedure can be performed at step 2508.

In accordance with the description above, methods and apparatuses for delivering patient information during a medical procedure have been illustrated and described. In the foregoing specification, specific embodiments of the present invention have been described. However, one of ordinary skill in the art appreciates that various modifications and changes can be made without departing from the scope of the present invention as set forth in the claims below. Thus, while preferred embodiments of the invention have been illustrated and described, it is clear that the invention is not so limited. Numerous modifications, changes, variations, substitutions, and equivalents will occur to those skilled in the art without departing from the spirit and scope of the present invention as defined by the following claims. Accordingly, the specification and figures are to be regarded in an illustrative rather than a restrictive sense, and all such modifications are intended to be included within the scope of present invention. The benefits, advantages, solutions to problems, and any element(s) that may cause any benefit, advantage, or solution to occur or become more pronounced are not to be construed as a critical, required, or essential features or elements of any or all the claims.

What is claimed is:

1. A tray configured to accommodate a Foley catheter, the tray comprising:
   a surface defining a single layer tray comprising at least two compartments separated by a barrier, the at least two compartments comprising:
      a first compartment supporting a first syringe and a second syringe at different heights based upon order of use in a Foley catheterization procedure;
      a second compartment to accommodate the Foley catheter; and
   the barrier separating the first compartment from the second compartment;
   the first compartment defining a lubricating jelly application chamber to lubricate the Foley catheter;
   further comprising a patient aid comprising post-procedure information, disposed on a first portion of the patient aid, for caring for the Foley catheter when applied to a patient.

2. The tray of claim 1, wherein a higher of the first syringe or the second syringe is for use in the Foley catheterization procedure before a lower of the first syringe or the second syringe.

3. The tray of claim 1, further comprising:
   a wrap disposed about the tray;
   liquid hand sanitizer; and
   a sealed bag disposed about the wrap;
   the liquid hand sanitizer disposed between at least a portion of the wrap and the sealed bag.

4. The tray of claim 1, further comprising:
   a wrap disposed about the tray;
   printed instructions for using the tray; and
   a sealed bag disposed about the wrap.

5. The tray of claim 4, the printed instructions to instruct application of the lubricating jelly disposed in one of the first syringe or the second syringe to the Foley catheter using the lubricating jelly application compartment.

6. The tray of claim 4, the printed instructions comprising one or more panels separated by one or more folds.

7. The tray of claim 4, the printed instructions comprising illustrations showing how to use the Foley catheter and corresponding medical devices on a patient.

8. The tray of claim 4, the printed instructions comprising suggestions for preventing catheter associated urinary tract infections.

9. The tray of claim 1, further comprising printed instructions instructing passage of a tip of the Foley catheter into lubricating jelly dispensed from one of the first syringe or the second syringe into the first compartment, thereby lubricating the tip of the Foley catheter.

10. A Foley catheter container, comprising:
    a single layer tray comprising a surface defining at least two compartments separated by a barrier, the at least two compartments comprising:
       a first compartment comprising a first compartment base member, the first compartment to accommodate a first syringe and a second syringe;

a second compartment comprising a second compartment base member;
the Foley catheter, situated in the second compartment;
the barrier separating the first compartment from the second compartment;
the first compartment base member situated at a different height within the tray than the second compartment base member;
the first compartment defining a lubricating jelly application chamber to lubricate the Foley catheter when passed from the second compartment into the first compartment of the single layer tray;
further comprising a patient aid comprising post-procedure information, disposed on a first portion of the patient aid, for caring for the Foley catheter applied to a patient.

11. The Foley catheter container of claim 10, further comprising:
a wrap disposed about the tray; and
a sealed bag disposed about the wrap.

12. The Foley catheter container of claim 11, further comprising liquid hand sanitizer disposed outside the at least a portion of the wrap and inside the sealed bag.

13. The tray of claim 10, further comprising:
a wrap disposed about the tray;
printed instructions for using the tray; and
a sealed bag disposed about the wrap.

14. The tray of claim 13, the printed instructions instructing dispensation of lubricating jelly from one of the first syringe or the second syringe into the first compartment and application of the lubricating jelly to the Foley catheter using the lubricating jelly application compartment.

15. A tray for a Foley catheter, comprising:
a single-layer surface defining at least two compartments separated by a barrier, the at least two compartments comprising:
a first compartment comprising a base member, the first compartment accommodating a first syringe and a second syringe;
a second compartment accommodating the Foley catheter; and
the barrier separating the first compartment from the second compartment;
the base member defining a mnemonic device indicating which of the first syringe or the second syringe should be used to dispense lubricating jelly disposed in one of the first syringe or the second syringe into the first compartment;
the first compartment defining a lubricating jelly application compartment to lubricate the Foley catheter with the lubricating jelly from the one of the first syringe or the second syringe when at least a portion of the Foley catheter is passed from the second compartment into the first compartment while remaining within a perimeter defined by the single-layer surface;
further comprising information, disposed on a first portion of a patient aid, for caring for the Foley catheter when applied to a patient.

16. The tray of claim 15, further comprising:
a wrap disposed about the tray; and
a sealed bag disposed about the wrap.

17. The tray of claim 15, further comprising:
a wrap disposed about the tray;
printed instructions for using the tray; and
a sealed bag disposed about the wrap.

18. The tray of claim 17, the printed instructions instructing dispensation of the lubricating jelly from the one of the first syringe or the second syringe into the first compartment and application of the lubricating jelly to the at least a portion of the Foley catheter using the lubricating jelly application compartment.

19. A single-layer tray, comprising:
a surface defining at least two compartments separated by a barrier, the at least two compartments comprising:
a first compartment to support a first syringe and a second syringe, the first compartment comprising one or more recesses for accommodating flanges of one or more of the first syringe or the second syringe;
a second compartment to accommodate a Foley catheter;
the first syringe and the second syringe, situated in the first compartment;
the Foley catheter, situated in the second compartment;
the barrier separating the first compartment from the second compartment;
the first compartment defining a lubricating jelly application chamber to lubricate the Foley catheter;
further comprising post-procedure information for caring for the Foley catheter when applied to a patient, wherein the post procedure information is disposed on a first portion of a patient aid.

20. The single-layer tray of claim 19, the first compartment further to support the first syringe and the second syringe in a non-parallel configuration.

21. The tray of claim 19, the first compartment further to support the first syringe and the second syringe so that a plunger of each syringe is predisposed to project upward and out of the tray.

22. The tray of claim 19, further comprising:
a wrap disposed about the tray;
printed instructions for using the tray; and
a sealed bag disposed about the wrap;
the printed instructions disposed between the wrap and the sealed bag.

23. The tray of claim 19, further comprising:
a wrap disposed about the tray; and
a sealed bag disposed about the wrap.

24. The tray of claim 23, further comprising liquid hand sanitizer disposed outside the at least a portion of the wrap and inside the sealed bag.

25. The tray of claim 23, further comprising printed instructions instructing application of lubricating jelly dispensed from the first syringe into the first compartment to at least a portion of the Foley catheter using the lubricating jelly application compartment.

* * * * *

(12) INTER PARTES REVIEW CERTIFICATE (2613th)
United States Patent (10) Number: US 9,795,761 K1
Lockwood et al. (45) Certificate Issued: Feb. 24, 2022

(54) MEDICAL KIT, PACKAGING SYSTEM, INSTRUCTION INSERT, AND ASSOCIATED METHODS

(75) Inventors: Robert Lockwood; Jennifer E. Tomes; Susan E. Macinnes; Sarah Zyburt

(73) Assignee: MEDLINE INDUSTRIES, INC.

Trial Number:

IPR2019-00109 filed Oct. 24, 2018

Inter Partes Review Certificate for:

Patent No.: 9,795,761
Issued: Oct. 24, 2017
Appl. No.: 13/153,265
Filed: Jun. 3, 2011

The results of IPR2019-00109 are reflected in this inter partes review certificate under 35 U.S.C. 318(b).

INTER PARTES REVIEW CERTIFICATE
U.S. Patent 9,795,761 K1
Trial No. IPR2019-00109
Certificate Issued Feb. 24, 2022

AS A RESULT OF THE INTER PARTES REVIEW PROCEEDING, IT HAS BEEN DETERMINED THAT:

Claims 1-19 and 22-25 are found patentable.

\* \* \* \* \*